United States Patent
Li et al.

(10) Patent No.: US 8,168,642 B2
(45) Date of Patent: May 1, 2012

(54) DIHYDROPYRIMIDINE COMPOUNDS AND THEIR USES IN PREPARATION OF MEDICAMENTS FOR TREATING AND PREVENTING ANTIVIRAL DISEASES

(75) Inventors: Song Li, Beijing (CN); Guoming Zhao, Beijing (CN); Guangqiang Xia, Beijing (CN); Lili Wang, Beijing (CN); Zhibing Zheng, Beijing (CN); Yunde Xie, Beijing (CN); Wu Zhong, Beijing (CN); Junhai Xiao, Beijing (CN); Xingzhou Li, Beijing (CN); Hao Cui, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 401 days.

(21) Appl. No.: 12/373,183

(22) PCT Filed: Jul. 9, 2007

(86) PCT No.: PCT/CN2007/002098
§ 371 (c)(1),
(2), (4) Date: Jun. 3, 2009

(87) PCT Pub. No.: WO2008/009209
PCT Pub. Date: Jan. 24, 2008

(65) Prior Publication Data
US 2010/0087448 A1 Apr. 8, 2010

(30) Foreign Application Priority Data
Jul. 10, 2006 (CN) .......................... 2006 1 0098646

(51) Int. Cl.
*C07D 239/20* (2006.01)
*C07D 403/04* (2006.01)
*A61K 31/506* (2006.01)

(52) U.S. Cl. .......................... 514/256; 544/333; 544/335
(58) Field of Classification Search .................. 544/333, 544/335; 514/256
See application file for complete search history.

(56) References Cited

U.S. PATENT DOCUMENTS
6,503,913 B1 * 1/2003 Goldmann et al. ............ 514/256
2004/0009991 A1 * 1/2004 Ohno et al. .................... 514/256

FOREIGN PATENT DOCUMENTS
| CN | 1297449 | 5/2001 |
|---|---|---|
| CN | 1305471 | 7/2001 |
| WO | WO 99/54329 A1 | 10/1999 |
| WO | WO 99/54326 A | 12/1999 |
| WO | WO 02/22588 A1 | 3/2002 |
| WO | WO 2006/009889 A1 | 1/2006 |

OTHER PUBLICATIONS

Razonable et al., PubMed Abstract (Herpes 10(3):60-5), Dec. 2003.*
Douglar, Jr. Introduction to Viral Diseases, Cecil Textbook of Medicine, 20th Edition, vol. 2, pp. 1739-1747, 1996.*
Goff, PubMed Abstract (J Gene Med. 3(6):517-28) Nov.-Dec. 2001.*
Bosseray et al., PubMed Abstract (Pathol. Biol. 50(8):483-92), Oct. 2002.*
Ulrich, Chapter 4: Crystal Characteristics, Kirk Othmer Encyclopedia of Chemical Technology (7 pages), Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
International Search Report—PCT/CN2007/002098—mailed on Sep. 6, 2007.
Lengar et al., "Tunable Carbon-Carbon and Carbon-Sulfur Cross-Coupling of Boronic Acids with 3,4-Dihydropyrimidine-2-thiones", *Organic Letters*, 2004, 6(5), p. 771-774.
Kuno et al., "Studies on Cerebral Protective Agents, I. Novel 4-aryl Pryimidine Derivatives with Anti-Anoxic and Anti-lipid Peroxidation Activities", *Chem. Pharm. Bull.*, 1992, 40(6), p. 1452-1461.
European Search Report for EP 07 76 4006, mailed Aug. 10, 2010.
Deres, Karl, "Inhibition of Hepatitis B Virus Replication by Drug-Induced Depletion of Nucleocapsids", *Science*, vol. 299 Feb. 7, 2009, pp. 893-896.

* cited by examiner

*Primary Examiner* — Deepak Rao
(74) *Attorney, Agent, or Firm* — Brinks Hofer Gilson & Lione

(57) ABSTRACT

The present invention relates to a compound of formula (I) or a pharmaceutically acceptable salt or hydrate thereof, to a process for preparing the compound of formula (I), and to use of the compound of formula (I) or a pharmaceutically acceptable salt or hydrate thereof as a medicament, in particular as a medicament for the treatment and prevention of type B hepatitis.

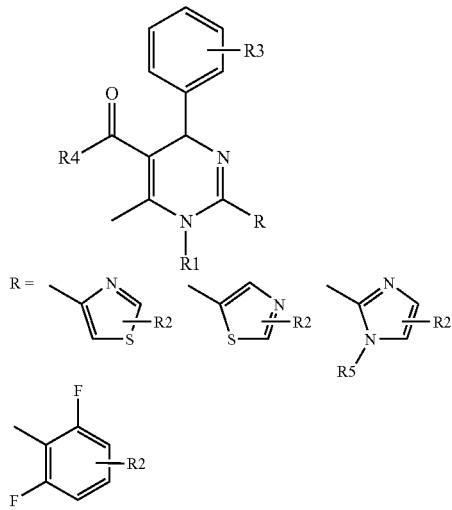

4 Claims, No Drawings

DIHYDROPYRIMIDINE COMPOUNDS AND THEIR USES IN PREPARATION OF MEDICAMENTS FOR TREATING AND PREVENTING ANTIVIRAL DISEASES

This application is a 371 of PCT/CN2007/002098 filed Jul. 9, 2007.

TECHNICAL FIELD

The present invention relates to a dihydropyrimidine compound of formula (I) and a process for preparing the same, a pharmaceutical composition comprising the same, as well as use of said compound or a pharmaceutically acceptable salt or a hydrate thereof as a medicament, in particular as a medicament for the treatment and prevention of type B hepatitis (HB).

BACKGROUND ART

Chronic type B hepatitis is a serious infectious disease caused by hepatitis B virus (HBV) and prevalent throughout the world, and is closely relevant to the occurrence of hepatic cirrhosis and liver cancer. China is a high-risk area of HB. The results of seroepidemiological survey of viral hepatitis in China from 1992 to 1995 indicated that the persons carrying the surface antigen (HBsAg) of hepatitis B virus in China accounted for 9.7% of the population, and it was estimated that about 130 millions persons were HBV carriers. A study on the epidemiological situation of viral hepatitis in China demonstrated that the annual reported incidence of HB was increased from 21.9/100 thousands in 1990 to 53.3/100 thousands in 2003, showing an obvious ascending tendency (Wang Xiaojun, Zhang Rongzhen, Hu Yuansheng, et al, Monitoring of Diseases, 2004, 19(8): 290-292). Chronic HB not only seriously affects human health, but also imposes heavy economic burden on a family and society. Therefore, Chronic HB has become one of significant public health concerns in China.

The drugs useful for treating chronic HB mainly include two types—immunomodulator and nucleoside inhibitor of DNA polymerase (Loomba R., Liang T. J., Antivir. Ther., 2006, 11(1): 1-15). The former includes: interferon-α2b (IFN-α2b, Intron A®) and PEGylated interferon-α2a (peg-IFN-α2a, Pegasys®); the latter includes: Lamivudine (Epivir-HBV®), Adefovir Dipivoxil (Hepsera®) and Entecavir (Baraclude®). Comparatively, the number and type of drugs available for treating HB in clinic are still limited. Thus, it is extremely important to continuously research and develop new safe and effective anti-virus drugs, in particular those having a completely new mechanism of action.

Deres et al. reported heteroaromatic ring substituted dihydropyrimidine (HAP) compounds represented by Bay41-4109 and Bay39-5493, which compounds could act to suppress the replication of HBV by preventing the normal formation of nucleocapsid. The preclinical data demonstrated that Bay41-4109 had relatively good drug metabolism parameters (Deres K., Schroder C. H., Paessens A., et al. Science, 2003, 299 (5608):893-896). A study on its mechanism of action showed that HAP changed the angle between dimers forming nucleocapsid, resulting in the formation of unstable swelled nucleocapsid, and accelerating the degradation of core protein by interacting with 113-143 amino acid residues of core protein (Hacker H. J., Deres K., Mildenberger M., et al., Biochem. Pharmacol. 2003, 66(12):2273-2279). WO99/54326 and WO99/54329 disclosed 2-pyridyl substituted and 2-thiazolyl substituted dihydropyrimidine compounds, respectively.

CONTENTS OF THE INVENTION

The present invention relates to a new dihydropyrimidine compound of formula (I)

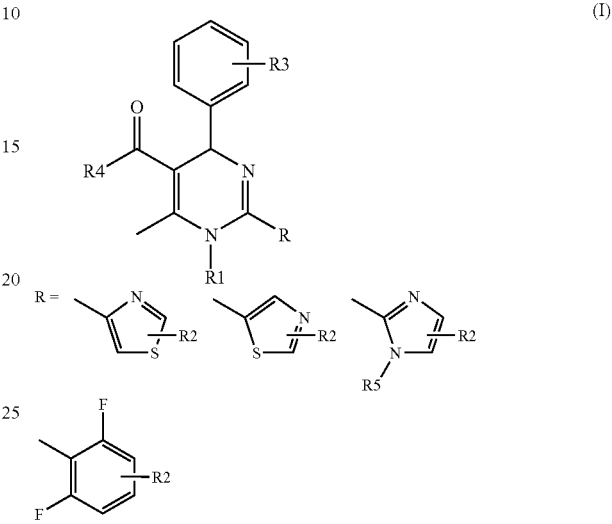

or a pharmaceutically acceptable salt or hydrate thereof, wherein $R^1$ represents hydrogen, $(C_1-C_4)$-alkyl, $(C_2-C_4)$-alkenyl, $(C_2-C_6)$-acyl or benzoyl, $R^2$ represents a mono- or multi-substituted, the same or different substitutent selected from: hydrogen, halogen, hydroxyl, cyano, trifluoromethyl, nitro, benzyl, $(C_1-C_6)$-alkyl, $(C_1-C_6)$-alkoxy, $(C_1-C_6)$-alkylthio, $(C_1-C_6)$-alkoxycarbonyl, $(C_1-C_6)$-acyloxy, amino, $(C_1-C_6)$-alkylamino or $(C_1-C_6)$-dialkylamino, $(C_1-C_6)$-acylamino, $R^3$ represents a mono- or multi-substituted, the same or different substituent selected from: hydrogen, halogen, trifluoromethyl, trifluoromethoxy, trifluoromethylsulfonyl, nitro, cyano, carboxy, hydroxyl, $(C_1-C_6)$-alkoxy, $(C_1-C_6)$-alkoxycarbonyl and $(C_1-C_6)$-alkyl, wherein said alkyl may be substituted by aryl having from 6 to 10 carbon atoms, halogen, or a group presented by formulae —S—$R^6$, $NR^7R^8$, CO—$NR^9R^{10}$ and -A-$CH_2$—$R^{11}$, wherein $R^6$ represents phenyl optionally substituted by halogen, $R^7$, $R^8$, $R^9$ and $R^{10}$, the same or different, respectively represent hydrogen, phenyl, hydroxyl-substituted phenyl, hydroxyl, $(C_1-C_6)$-acyl or $(C_1-C_6)$-alkyl, wherein said alkyl may be substituted by hydroxyl, halogen, $(C_1-C_6)$-alkoxycarbonyl, phenyl or hydroxyl-substituted phenyl, A represents O, S, SO or $SO_2$, $R^{11}$ represents phenyl optionally mono- or multi-substituted by a same or different group selected from: halogen, nitro, trifluoromethyl, $(C_1-C_6)$-alkyl and $(C_1-C_6)$-alkoxy, $R^4$ represents a group represented by formula —$XR^{12}$ or —$NR^{13}R^{14}$, wherein X represents oxygen or a bond, $R^{12}$ represents hydrogen, a straight or branched $(C_1-C_6)$-alkoxycarbonyl, or a straight, branched or cyclic saturated or unsaturated $(C_1-C_8)$-hydrocarbyl, wherein said hydrocarbyl optionally comprises one or two identical or different heterochain unit(s) selected from the group consisting of O, CO, NH, —NH($C_1$-$C_4$)-alkyl, —N(($C_1$-$C_4$)-alkyl)$_2$, S and $SO_2$, and is optionally substituted by halogen, nitro, cyano, hydroxyl, aryl having from 6 to 10 carbon atoms, aralkyl, heteroaryl or a group represented by formula —$NR^{15}R^{16}$, wherein $R^{15}$ and $R^{16}$, the same or different, respectively represent hydrogen, benzyl or ($C_1$-$C_6$)-alkyl, $R^{13}$ and $R^{14}$, the same or different, respectively represent hydrogen, benzyl, ($C_1$-$C_6$)-alkyl, or cycloalkyl having from 3 to 6 carbon atoms, $R^5$ represents hydrogen, benzyl, ($C_1$-$C_6$)-alkyl, wherein said alkyl may be substituted by hydroxyl, halogen, ($C_1$-$C_6$)-alkoxycarbonyl, phenyl or substituted phenyl.

The term "($C_2$-$C_6$)-alkenyl" as used herein refers to a straight or branched alkenyl having from 2 to 6 carbon atoms, preferably a straight or branched alkenyl having from 3 to 5 carbon atoms, including, but not limited to, vinyl, propenyl, n-pentenyl, n-hexenyl.

The term "($C_2$-$C_6$)-acyl" as used herein refers to a straight or branched acyl having from 2 to 6 carbon atoms, preferably a straight or branched acyl having from 2 to 4 carbon atoms.

The term "aryl" as used herein usually refers to a 5- to 14-membered substituted or unsubstituted aryl ring system, or an aryl ring system comprising a fused bicycle or tricycle, including, but not limited to, phenyl and naphthyl.

The term "($C_1$-$C_6$)-alkyl" as used herein refers to a straight or branched radical having from 1 to 6 carbon atoms, including, but not limited to methyl, ethyl, n-propyl, isopropyl, n-butyl, sec-butyl, isobutyl, t-butyl, and the like.

The term "($C_1$-$C_6$)-alkoxy" as used herein refers to a straight or branched alkoxy having from 1 to 6 carbon atoms, preferably a straight or branched alkoxy having from 1 to 4 carbon atoms, including, but not limited to methoxy, ethoxy, propoxy, isopropoxy, butoxy, isobutoxy, t-butoxy, and the like.

The term "($C_1$-$C_6$)-alkylthio" as used herein refers to a straight or branched alkylthio having from 1 to 6 carbon atoms, preferably a straight or branched alkylthio having from 1 to 4 carbon atoms.

The term "($C_1$-$C_6$)-alkoxycarbonyl" as used herein refers to a straight or branched alkoxycarbonyl having from 1 to 6 carbon atoms, preferably a straight or branched alkoxycarbonyl having from 1 to 4 carbon atoms, including, but not limited to methoxycarbonyl, ethoxycarbonyl, propoxycarbonyl, isopropoxycarbonyl, butoxycarbonyl, isobutoxycarbonyl, t-butoxycarbonyl, and the like.

The compound of the present invention includes a compound of formula (I) and its isomer Ia and a mixture thereof. If $R^1$ is hydrogen, isomers I and Ia exist in tautomeric equilibrium:

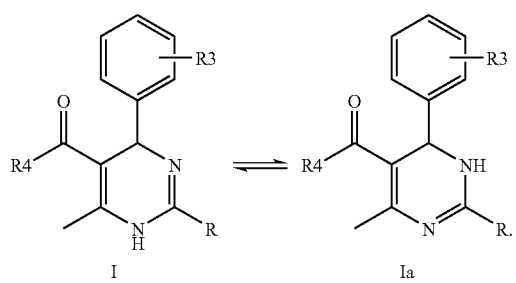

The compound of the present invention may exist in a stereomeric form, and said stereomeric forms are in enantiomeric or diastereoisomeric relationship. The present invention relates to these enantiomers or diastereoisomers or a mixture thereof. Like a diastereoisomer, a racemate may be resolved into a single stereomer by using known methods.

The compound of the present invention may also be in the form of a salt. Its pharmaceutically acceptable salt is preferred.

The pharmaceutically acceptable salt includes, but not limited to, salts formed with various inorganic acids such as hydrochloric acid, sulfuric acid, phosphoric acid, phosphorous acid, hydrobromic acid and nitric acid, and salts formed with various organic acids such as maleic acid, fumaric acid, malic acid, succinic acid, tartaric acid, citric acid, acetic acid, lactic acid, benzoic acid, methanesulfonic acid, ethanesulfonic acid, benzenesulfonic acid, p-toluenesulfonic acid, palmic acid and etc.

The pharmaceutically acceptable salt further includes, but not limited to, metal salts of the compound of the present invention, such as sodium salt, potassium salt, magnesium salt or calcium salt, or ammonium salts formed with ammonia or an organic amine such as ethylamine, diethylamine, triethylamine, diethanolamine, triethanolamine, dicyclohexylamine, dimethylaminoethanol, arginine, lysine, ethylenediamine, or 2-phenylethylamine, and the like.

Some compounds in the present invention may be crystallized or recrystallized by using water or various organic solvents, and in this case, various solvates may be formed. The present invention includes those stoichiometric solvates, hydrates, and also compounds comprising variable amount of water formed when prepared using lyophilisation.

The compounds of formula (I) as defined below and their salts or hydrates are preferred, wherein:

$R^1$ represents hydrogen, methyl, benzoyl or acetyl, $R^2$ represents a mono- or multi-substituted, the same or different substituent selected from: hydrogen, fluoro, chloro, bromo, benzyl, ($C_1$-$C_4$)-alkyl, ($C_1$-$C_4$)-alkoxy, amino, ($C_1$-$C_4$)-acylamino, $R^3$ represents a mono- or multi-substituted, the same or different substituent selected from: hydrogen, halogen, trifluoromethyl, trifluoromethoxy, trifluoromethylsulfonyl, nitro, cyano, carboxy, hydroxyl, methoxycarbonyl and a group represented by formula —$CONHCH_2C(CH_3)_3$, —$CONH(CH_2)_2OH$, —$CONHCH_2C_6H_5$, —$CONHC_6H_5$, —$OCH_2C_6H_5$ or —S-pCl—$C_6H_4$, $R^4$ represents a group represented by formula —$XR^{12}$ or —$NR^{13}R^{14}$, wherein X represents oxygen or a bond, $R^{12}$ represents hydrogen, ($C_1$-$C_4$)-alkenyl, ($C_1$-$C_4$)-alkoxycarbonyl or ($C_1$-$C_4$)-alkyl, wherein the radical may be optionally substituted by pyridyl, cyano, phenoxy, hydroxyl, trifluoroethyl, benzyl or a group represented by formula —$NR^{15}R^{16}$, wherein $R^{15}$ and $R^{16}$, the same or different, respectively represent hydrogen, benzyl or ($C_1$-$C_4$)-alkyl, $R^{13}$ and $R^{14}$, the same or different, respectively represent hydrogen, benzyl, ($C_1$-$C_4$)-alkyl, or cyclopropyl, $R^5$ represents hydrogen, benzyl, ($C_1$-$C_6$)-alkyl, wherein said alkyl may be substituted by hydroxyl, chloro, fluoro, ($C_1$-$C_3$)-alkoxycarbonyl, phenyl or substituted phenyl.

The compounds of formula (I) as defined below and their salts or hydrates are preferred, wherein:

$R^1$ represents hydrogen, methyl, benzoyl or acetyl, $R^2$ represents a mono- or multi-substituted, the same or different substituent selected from: hydrogen, fluoro, chloro, bromo, benzyl, $(C_1-C_3)$-alkyl, $(C_1-C_3)$-alkoxy, amino, $(C_1-C_3)$-acylamino, $R^3$ represents a mono- or multi-substituted, the same or different substituent selected from: hydrogen, fluoro, chloro, bromo, iodo, hydroxyl, trifluoromethyl, trifluoromethoxy, trifluoromethylsulfonyl, nitro, cyano, carboxy, methoxycarbonyl and a group represented by formula —$CONHCH_2C(CH_3)_3$, —$CONH(CH_2)_2OH$, —$CONHCH_2C_6H_5$, —$CONHC_6H_5$, —$OCH_2C_6H_5$ or —$S\text{-}pCl\text{-}C_6H_4$, $R^4$ represents a group represented by formula —$XR^{12}$ or —$NR^{13}R^{14}$, wherein X represents oxygen or a bond, $R^{12}$ represents hydrogen, $(C_1-C_3)$-alkenyl, $(C_1-C_4)$-alkoxycarbonyl or $(C_1-C_4)$-alkyl, wherein the radical may be optionally substituted by pyridyl, cyano, phenoxy, hydroxyl, trifluoroethyl, benzyl or a group represented by formula —$NR^{15}R^{16}$, wherein $R^{15}$ and $R^{16}$, the same or different, respectively represent hydrogen, benzyl or methyl, $R^{13}$ and $R^{14}$, the same or different, respectively represent hydrogen, benzyl, $(C_1-C_3)$-alkyl, or cyclopropyl, $R^5$ represents hydrogen, benzyl, $(C_1-C_3$-alkyl, wherein said alkyl may be substituted by hydroxyl, chloro, fluoro, methoxycarbonyl, or ethoxycarbonyl.

The compounds of formula (I) as defined below and their salts or hydrates are particularly preferred, wherein:

$R^1$ represents hydrogen or acetyl, $R^2$ represents a mono- or multi-substituted, the same or different substituent selected from: hydrogen, fluoro, chloro, methyl, amino, or acetylamino, $R^3$ represents a mono- or multi-substituted, the same or different substituent selected from: hydrogen, fluoro, chloro, bromo, hydroxyl, nitro, methoxy, or methyl, $R^4$ represents a group represented by formula —$XR^{12}$ or —$NR^{13}R^{14}$, wherein X represents oxygen, $R^{12}$ represents a straight or branched alkyl having up to 3 carbon atoms, $R^{13}$ and $R^{14}$ respectively represent hydrogen, α-methylbenzyl, $R^5$ represents hydrogen, methyl, or benzyl.

The particularly preferred compound of formula (I) of the present invention is selected from the group consisting of:

(1) Ethyl 2-(thiazol-4-yl)-4-(2-chloro-4-fluorophenyl)-6-methyl-1,4-dihydro-pyrimidin-5-carboxylate;
(2) Ethyl 2-(thiazol-4-yl)-4-(3-fluorophenyl)-6-methyl-1,4-dihydro-pyrimidin-5-carboxylate;
(3) Ethyl 2-(thiazol-4-yl)-4-(4-fluorophenyl)-6-methyl-1,4-dihydro-pyrimidin-5-carboxylate;
(4) Ethyl 2-(thiazol-4-yl)-4-(3-methylphenyl)-6-methyl-1,4-dihydro-pyrimidin-5-carboxylate;
(5) Ethyl 2-(thiazol-4-yl)-4-(4-methylphenyl)-6-methyl-1,4-dihydro-pyrimidin-5-carboxylate;
(6) Ethyl 2-(thiazol-4-yl)-4-(3-methoxyphenyl)-6-methyl-1,4-dihydro-pyrimidin-5-carboxylate;
(7) Ethyl 1-acetyl-2-(thiazol-4-yl)-4-(3-methoxyphenyl)-6-methyl-1,4-dihydro-pyrimidin-5-carboxylate;
(8) Ethyl 2-(thiazol-4-yl)-4-(4-methoxyphenyl)-6-methyl-1,4-dihydro-pyrimidin-5-carboxylate;
(9) Ethyl 2-(thiazol-4-yl)-4-(3-hydroxyphenyl)-6-methyl-1,4-dihydro-pyrimidin-5-carboxylate;
(10) Ethyl 2-(thiazol-4-yl)-4-(4-hydroxyphenyl)-6-methyl-1,4-dihydro-pyrimidin-5-carboxylate;
(11) Ethyl 2-(thiazol-4-yl)-4-(3-chlorophenyl)-6-methyl-1,4-dihydro-pyrimidin-5-carboxylate;
(12) Ethyl 2-(thiazol-4-yl)-4-(2-fluorophenyl)-6-methyl-1,4-dihydro-pyrimidin-5-carboxylate;
(13) Ethyl 2-(thiazol-4-yl)-4-(4-chlorophenyl)-6-methyl-1,4-dihydro-pyrimidin-5-carboxylate;
(14) Ethyl 2-(thiazol-4-yl)-4-phenyl-6-methyl-1,4-dihydro-pyrimidin-5-carboxylate;
(15) Ethyl 2-(2-methylthiazol-4-yl)-4-(2-chloro-4-fluorophenyl)-6-methyl-1,4-dihydro-pyrimidin-5-carboxylate;
(16) Ethyl 2-(2-methylthiazol-4-yl)-4-(3-hydroxyphenyl)-6-methyl-1,4-dihydro-pyrimidin-5-carboxylate;
(17) Ethyl 2-(2-methylthiazol-4-yl)-4-(4-hydroxyphenyl)-6-methyl-1,4-dihydro-pyrimidin-5-carboxylate;
(18) Ethyl 2-(2-methylthiazol-4-yl)-4-(3-chlorophenyl)-6-methyl-1,4-dihydro-pyrimidin-5-carboxylate;
(19) Ethyl 1-acetyl-2-(2-methylthiazol-4-yl)-4-(3-fluorophenyl)-6-methyl-1,4-dihydro-pyrimidin-5-carboxylate;
(20) Ethyl 1-acetyl-2-(2-methylthiazol-4-yl)-4-(4-fluorophenyl)-6-methyl-1,4-dihydro-pyrimidin-5-carboxylate;
(21) Ethyl 1-acetyl-2-(2-methylthiazol-4-yl)-4-(3-methylphenyl)-6-methyl-1,4-dihydro-pyrimidin-5-carboxylate;
(22) Ethyl 1-acetyl-2-(2-methylthiazol-4-yl)-4-(4-methylphenyl)-6-methyl-1,4-dihydro-pyrimidin-5-carboxylate;
(23) Ethyl 1-acetyl-2-(2-methylthiazol-4-yl)-4-(3-methoxyphenyl)-6-methyl-1,4-dihydro-pyrimidin-5-carboxylate;
(24) Ethyl 1-acetyl-2-(2-methylthiazol-4-yl)-4-(4-methoxyphenyl)-6-methyl-1,4-dihydro-pyrimidin-5-carboxylate;
(25) Ethyl 1-acetyl-2-(2-methylthiazol-4-yl)-4-phenyl-6-methyl-1,4-dihydro-pyrimidin-5-carboxylate;
(26) Ethyl 1-acetyl-2-(2-methylthiazol-4-yl)-4-(4-chlorophenyl)-6-methyl-1,4-dihydro-pyrimidin-5-carboxylate;
(27) Ethyl 1-acetyl-2-(2-methylthiazol-4-yl)-4-(2-chloro-4-fluorophenyl)-6-methyl-1,4-dihydro-pyrimidin-5-carboxylate;
(28) Methyl 2-(thiazol-4-yl)-4-(2-chloro-4-fluorophenyl)-6-methyl-1,4-dihydro-pyrimidin-5-carboxylate;
(29) Methyl 2-(2-methylthiazol-4-yl)-4-(2-chloro-4-fluorophenyl)-6-methyl-1,4-dihydro-pyrimidin-5-carboxylate;
(30) Ethyl 2-(2-acetylaminothiazol-4-yl)-4-(2-chloro-4-fluorophenyl)-6-methyl-1,4-dihydro-pyrimidin-5-carboxylate;
(31) Ethyl 2-(2-aminothiazol-4-yl)-4-(2-chloro-4-fluorophenyl)-6-methyl-1,4-dihydro-pyrimidin-5-carboxylate;
(32) Ethyl 2-(5-chlorothiazol-4-yl)-4-(2-chloro-4-fluorophenyl)-6-methyl-1,4-dihydro-pyrimidin-5-carboxylate;
(33) Ethyl 2-(2-chlorothiazol-4-yl)-4-(2-chloro-4-fluorophenyl)-6-methyl-1,4-dihydro-pyrimidin-5-carboxylate;
(34) Methyl 2-(2-chlorothiazol-4-yl)-4-(2-chloro-4-fluorophenyl)-6-methyl-1,4-dihydro-pyrimidin-5-carboxylate;
(35) Methyl 2-(5-chlorothiazol-4-yl)-4-(2-chloro-4-fluorophenyl)-6-methyl-1,4-dihydro-pyrimidin-5-carboxylate;
(36) Methyl 2-(5-chlorothiazol-4-yl)-4-(4-fluorophenyl)-6-methyl-1,4-dihydro-pyrimidin-5-carboxylate;

(37) Methyl 2-(4-methylthiazol-5-yl)-4-(2-chloro-4-fluorophenyl)-6-methyl-1,4-dihydro-pyrimidin-5-carboxylate;
(38) Ethyl 2-(4-methylthiazol-5-yl)-4-(2-chloro-4-fluorophenyl)-6-methyl-1,4-dihydro-pyrimidin-5-carboxylate;
(39) Methyl 2-(2,4-dimethylthiazol-5-yl)-4-(2-chloro-4-fluorophenyl)-6-methyl-1,4-dihydro-pyrimidin-5-carboxylate;
(40) Ethyl 2-(2,4-dimethylthiazol-5-yl)-4-(2-chloro-4-fluorophenyl)-6-methyl-1,4-dihydro-pyrimidin-5-carboxylate;
(41) Ethyl 2-(2-methylthiazol-5-yl)-4-(2-chloro-4-fluorophenyl)-6-methyl-1,4-dihydro-pyrimidin-5-carboxylate;
(42) Ethyl 2-(thiazol-5-yl)-4-(2-chloro-4-fluorophenyl)-6-methyl-1,4-dihydro-pyrimidin-5-carboxylate;
(43) Ethyl 2-(2-acetylaminothiazol-5-yl)-4-(2-chloro-4-fluorophenyl)-6-methyl-1,4-dihydro-pyrimidin-5-carboxylate;
(44) Ethyl 2-(2-aminothiazol-5-yl)-4-(2-chloro-4-fluorophenyl)-6-methyl-1,4-dihydro-pyrimidin-5-carboxylate;
(45) Ethyl 2-(2-chlorothiazol-5-yl)-4-(2-chloro-4-fluorophenyl)-6-methyl-1,4-dihydro-pyrimidin-5-carboxylate;
(46) Methyl 2-(2-chlorothiazol-5-yl)-4-(2-chloro-4-fluorophenyl)-6-methyl-1,4-dihydro-pyrimidin-5-carboxylate;
(47) Methyl 2-(2-chlorothiazol-5-yl)-4-(4-fluorophenyl)-6-methyl-1,4-dihydro-pyrimidin-5-carboxylate;
(48) Ethyl 2-(1H-imidazol-2-yl)-4-(2-chloro-4-fluorophenyl)-6-methyl-1,4-dihydro-pyrimidin-5-carboxylate;
(49) Ethyl 2-(N-methyl-1H-imidazol-2-yl)-4-(2-chloro-4-fluorophenyl)-6-methyl-1,4-dihydro-pyrimidin-5-carboxylate;
(50) Ethyl 2-(N-benzyl-1H-imidazol-2-yl)-4-(2-chloro-4-fluorophenyl)-6-methyl-1,4-dihydro-pyrimidin-5-carboxylate;
(51) Ethyl 2-(N-benzyl-1H-imidazol-2-yl)-4-(4-fluorophenyl)-6-methyl-1,4-dihydro-pyrimidin-5-carboxylate;
(52) Ethyl 2-(N-methyl-1H-imidazol-2-yl)-4-(2-chlorophenyl)-6-methyl-1,4-dihydro-pyrimidin-5-carboxylate;
(53) Ethyl 2-(N-methyl-1H-imidazol-2-yl)-4-(4-fluorophenyl)-6-methyl-1,4-dihydro-pyrimidin-5-carboxylate;
(54) Ethyl 2-(1H-imidazol-2-yl)-4-(2-chlorophenyl)-6-methyl-1,4-dihydro-pyrimidin-5-carboxylate;
(55) Methyl 2-(2,6-difluorophenyl)-4-(2-chloro-4-fluorophenyl)-6-methyl-1,4-dihydro-pyrimidin-5-carboxylate;
(56) Ethyl 2-(2,6-difluorophenyl)-4-(2-chloro-4-fluorophenyl)-6-methyl-1,4-dihydro-pyrimidin-5-carboxylate;
(57) Isopropyl 2-(2,6-difluorophenyl)-4-(2-chloro-4-fluorophenyl)-6-methyl-1,4-dihydro-pyrimidin-5-carboxylate;
(58) Ethyl 2-(2,4,6-trifluorophenyl)-4-(2-chloro-4-fluorophenyl)-6-methyl-1,4-dihydro-pyrimidin-5-carboxylate;
(59) Methyl 2-(2,4,6-trifluorophenyl)-4-(2-chloro-4-fluorophenyl)-6-methyl-1,4-dihydro-pyrimidin-5-carboxylate;
(60) R,R-N-(1-phenylethyl)-4-(2-chloro-4-fluorophenyl)-2-(2,4,6-trifluorophenyl)-6-methyl-1,4-dihydro-pyrimidin-5-carboxamide;
(61) R,R-N-(1-phenylethyl)-N-1-acetyl-4-(2-chloro-4-fluorophenyl)-2-(2,4,6-trifluorophenyl)-6-methyl-1,4-dihydro-pyrimidin-5-carboxamide; and
(62) Ethyl 4-R-(2-chloro-4-fluorophenyl)-2-(2,4,6-trifluorophenyl)-6-methyl-1,4-dihydro-pyrimidin-5-carboxylate,
or its pharmaceutically acceptable salt or hydrate.

The compound of formula (I) in the present invention may be prepared by the following process:

A) under the condition of adding a base or acid or not, and in a suitable inert solvent, reacting an amidine of formula (II) or a salt thereof

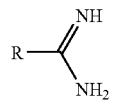
(II)

wherein R is defined as above, with an aldehyde of formula (III)

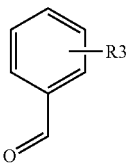
(III)

wherein $R^3$ is defined as above, and a compound of formula (IV)

$$CH_3CO-CH_2-CO-R^4 \quad (IV)$$

wherein $R^4$ is defined as above, or

B) under the condition of adding a base or acid or not, at a temperature of 20-150° C., and in a suitable inert solvent, reacting a compound of formula (V) or (VI)

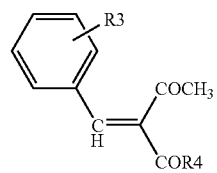
(V)

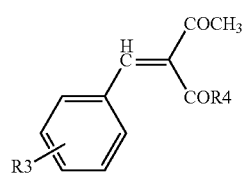
(VI)

wherein $R^3$, $R^4$ are as defined above, with the compound of formula (II), or C) reacting an aldehyde of formula (III)

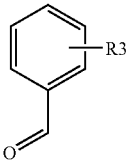
(III)

wherein $R^3$ is defined as above, with a compound of formula (VII)

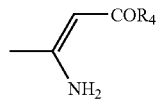

(VII)

wherein R⁴ is defined as above, and the amidine of formula (II), or

D) in the presence of an ammonium salt, reacting the aldehyde of formula (III) with the compound of formula (IV) and an iminoether of formula (VIII)

(VIII)

wherein R is defined as above, and R' is $C_1$-$C_4$ alkyl.

The compound, wherein $R^1$ is acetyl, can be prepared by reacting the compound obtained according to the above process, with acetyl chloride or acetic anhydride in an inert solvent in the presence of an inorganic base or an organic base at a temperature of 20-150° C.

The process of the present invention is exemplified by using the following reaction schemes:

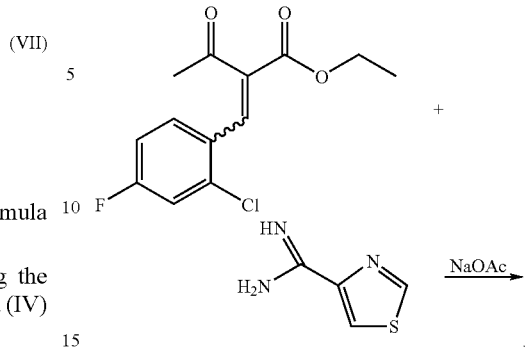

[A]

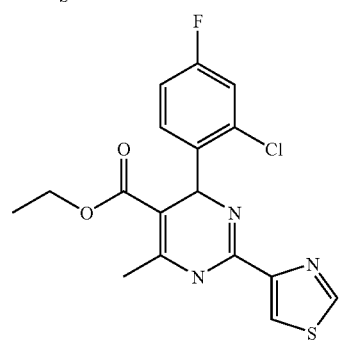

[B]

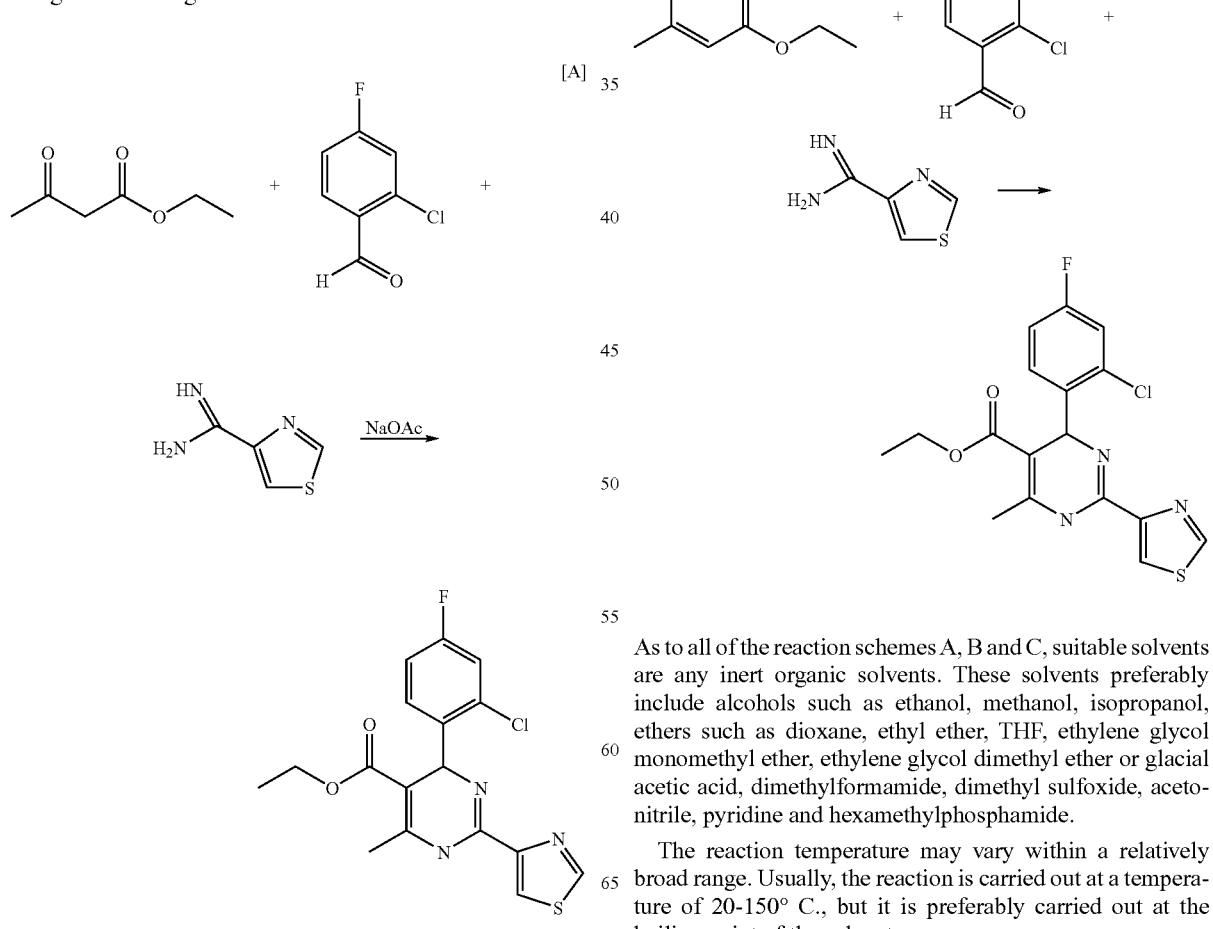

[C]

As to all of the reaction schemes A, B and C, suitable solvents are any inert organic solvents. These solvents preferably include alcohols such as ethanol, methanol, isopropanol, ethers such as dioxane, ethyl ether, THF, ethylene glycol monomethyl ether, ethylene glycol dimethyl ether or glacial acetic acid, dimethylformamide, dimethyl sulfoxide, acetonitrile, pyridine and hexamethylphosphamide.

The reaction temperature may vary within a relatively broad range. Usually, the reaction is carried out at a temperature of 20-150° C., but it is preferably carried out at the boiling point of the solvent.

The reaction may be carried out under normal pressure, or under an elevated pressure. Usually, the reaction is carried out under normal pressure.

The reaction may be carried out under the condition of adding a base or acid or not, but it is preferably carried out in the presence of a relatively weak acid such as acetic acid or formic acid.

The amidine of formula (II) as the starting substance is known in certain cases, or may be prepared from the corresponding cyano compound according to known methods described in literatures (cf. Diana, G. D., Yarinsky, A., Zalay, E. S., et al. J. Med. Chem. 1969, 12(9):791-793; Garigipati, R. S. Tetrahedron. Lett. 1990, 31(14):1969-1972; Boere, R. J., Oakley, R. T., Read, R. V. J Organometal. Chem. 1987, 331: 161-167; Judkins, B. D., Allen, D. G., Cook, T. A. Synth. Commun. 1996, 26(23):4351-4367; Tommasi, R. A., Macchia, W. M., Parker, D. T. Tetrahedron. Lett. 1998, 39:5947-5950).

The aldehyde of formula (III) as the starting substance is known, or may be prepared according to known methods described in literatures (cf. T. D. Harris and G. P. Roth, J. Org. Chem. 1979, 44, 146; DE 2165260, July 1972; DE 2401665, July 1974; Mijano et. al. CA 1963, 59, 13929c; E. Adler, H. D. Becker, Chem. Scand. 1961, 15, 849; E. P. Papadopoulos, M. Mardin, Ch. Issidoridis, J. Org. Chem. Soc. 1956, 78, 2543).

The β-keto carboxylate of formula (IV) as the starting substance is known, or may be prepared according to known methods described in literatures (cf. D. Berman: Reaction of Diketene with Alcohol, Phenol and Thiol, Houben-Weyl, Methods of Organic Chemistry, Vol. VII, pages 230-(1968); Y. Oikawa, K. sugano, O. Yonemitsu, J. Org. Chem. 1978, 43, 2087).

The stibylene-β-ketone ester of formula (V) or formula (VI) as the starting substance may be prepared according to known methods described in literatures (cf. G Jones, "Knoevenage Condensation", Organic Reaction, Vol. XV, pages 204-(1967)).

The enamino carboxylate of formula (VII) and iminoether of formula (VIII) as the starting substances are known, or may be prepared according to known methods described in literatures (cf. S. A. Glckman, A. C. Cope, J. Am. Chem. Soc. 1945, 67, 1017).

The compound of formula (I) in the present invention may be synthesized individually according to conventional method, or synthesized by libraries (each library includes at least two, or 5-1,000, optimally 10-100 compounds) according to mix-split method or parallel synthetic method of combinatorial chemistry, i.e., the compound may be synthesized according to a liquid phase method or a solid phase method.

As for more detailed information about the preparation of the compound of formula (I), please see the examples.

The antiviral effect of the compound of the present invention is determined according to the methods described by Sells, et al (M. A. Sells, M. L. Chen, G. Proc. Natl. Acad. Sci. 1987, 84, 1005-1009) and Korba, et al (B. E. Korba, J. L. Gerin Antiviral Research 1992, 19, 55-70).

The antiviral test was carried out in a 96-cell microtiter plate. The first column of the plate only contained a culture medium and HepG 2.2.15 cells, as a blank control.

First, a stock solution (50 mmol) of a test compound was dissolved in DMSO, and further diluted with a culture medium for growth of HepG 2.2.15 cells. Usually, the compound of the present invention was transferred by suction at a test concentration of 100 μg/ml (the first test concentration) to each cell of the second column of the microtiter plate, and then diluted with the culture medium for growth plus 2% fetal bovine serum (25 μL), by 2 times once, up to $2^{10}$ times at the maximum.

Then, 225 μL of a suspension of HepG 2.2.15 cells in the culture medium for growth plus 2% fetal bovine serum ($5 \times 10^4$ cells/ml) was added to each cell of the 96-cell microtiter plate.

The test mixture was incubated under the conditions of 37° C., 5% $CO_2$ for 4 days. Then, the supernatant was removed by suction, and to each cell 225 μL of a new-prepared culture medium for growth was added. Again, the compound of the present invention was added with a solution of 25 μL. The obtained mixture was further incubated for 4 days.

Prior to collection of the supernatant for determination of the antiviral effect, the change in cytotoxicity of HepG 2.2.15 cells was investigated by using optical microscopic technique or biochemical detection method (e.g., Alamar Blue staining or Trypan Blue staining).

Thereafter, the supernatant was collected, and sucked in vacuum to a 96-cell dot blot chamber covered by nylon film (used in accordance with the instructions for use provided by the manufacturer).

Determination of Cytotoxicity

The substance-induced change in cytotoxicity in HepG 2.2.15 cells or in inhibition of the cells could be determined by using, e.g., optical microscopic technique, and expressed by the change of cell morphology. Such substance-induced changes, e.g., cell lysis, cavity formation or change in cell morphology, in HepG 2.2.15 cells were apparent as compared to the untreated cells.

Taking the observed pathological change of cells as index, the pathological change of cells was observed under microscope after 8 days, a complete destroy being indicated as 4; 75% being indicated as 3; 50% being indicated as 2; 25% being indicated as 1; and no pathological change being indicated as 0. The average extents of pathological change of cells and the inhibition percentages at various concentrations were calculated. According to Reed&Muench method, a half toxic concentration ($TC_{50}$) and a maximum non-toxic concentration ($TC_0$) were calculated.

$TC_{50}$ refers to the concentration of the compound of the present invention when 50% of cells have a similar morphology to the corresponding cells as a control.

Determination of Antiviral Activity

After the supernatant was transferred onto the nylon film of the dot blot device (see the contents hereinabove), the supernatant of HepG 2.2.15 cells was denaturated (1.5 M NaCl/0.5 M NaOH), neutralized (3 M NaCl/0.5 M Tris. HCl, pH 7.5) and washed (2×SSC). Then, the filter film was kept at 120° C. for 2-4 hours, whereby DNA was baked on the filter film.

DNA Hybridization

Usually, viral DNA of HepG 2.2.15 cells treated on the nylon film was detected by using a non-radioactive digoxigenin labeled HB-specific DNA probe. Wherein, each time the probe was labeled with digoxigenin, purified and hybridized according to the directions for use given by the manufacturer.

Briefly, pre-hybridization and hybridization were conducted with 5×SSC, 1× blocking agent, 0.1% N-lauroyl sarcosine, 0.02% SDS and 100 μg sperm DNA of black carp. After pre-hybridization at 60° C. for 30 min, a specific hybridization (at 60° C. for 14 hr) was conducted with 20-40 ng/ml digoxigenin labeled denaturalized HBV specific DNA. Then, the film was washed, followed by HBV DNA detection with digoxigenin antibody.

The immunology detection of digoxigenin labeled DNA was conducted according to the directions for use given by the manufacturer.

Briefly speaking, the film was washed and pre-hybridized with a blocking agent (in accordance with the directions for use given by the manufacturer), and then hybridized with an anti-DIG antibody that had been previously coupled onto an alkaline phosphatase for 30 min. After washing, an alkaline phosphatase substrate CSPD was added, and cultured together with the filter for 5 min, and then wrapped in a plastic film, followed by further culturing at 37° C. for 15 min. The filter was exposed to X-ray, and the chemical luminous signal (culturing for 10 min to 2 hr according to the signal strength) of HB-specific DNA on the film was detected, whereby a half inhibitory concentration ($IC_{50}$) was calculated.

The half inhibitory concentration ($IC_{50}$) refers to the concentration of the compound of the present invention which reduces the HB-specific band by 50% as compared with the untreated sample.

The compound of the present invention exhibits a relatively strong antiviral effect. This kind of compound has unexpected antiviral activity to HBV, and thus is adapted to be used for treating various virus-caused diseases, in particular acute and chronic permanent diseases caused by HBV viral infection. Chronic viral diseases caused by HBV may lead to various syndromes having different extents of severity. As well known, chronic HBV infection may lead to hepatic cirrhosis and (or) liver cell carcinoma.

Examples of indications capable of being treated by the compound of the present invention include: acute and chronic viral infections capable of leading to infectious hepatitis, such as HB viral infection, and particularly preferred chronic HB viral infection and acute HB viral infection.

The pharmaceutical composition comprising the compound of the present invention may be administered in any of the following routes: orally, inhaled by spray, rectally, nasally, vaginally, topically, parenterally such as subcutaneous, intravenous, intramuscular, intraperitoneal, intrathecal, intraventricular, intrasternal or intracranial injection or infusion, or administered with the aid of an explanted reservoir, wherein the administration routes by orally, intramuscular, intraperitoneal or intravenous injection are preferred.

The compound of the present invention or the pharmaceutical composition comprising the compound of the present invention may be administered in a unit dosage form. The dosage form may be in a liquid form, or a solid form. The liquid form includes true solution, colloids, particulates, emulsions, suspensions. Other dosage forms include tablets, capsules, dropping pills, aerosols, pills, powder, solutions, suspensions, emulsions, granules, suppository, lyophilized powder for injection, clathrates, implants, patches, liniment, and the like.

The pharmaceutical composition of the present invention may further comprise a commonly used carrier that includes, but not limited to, ion exchanger, alumina, aluminum stearate, lecithin, serum protein such as human serum protein, buffer substance such as phosphate, glycerin, sorbic acid, potassium sorbate, a mixture of partial glycerine esters of saturated vegetable fatty acids, water, salt or electrolyte, such as protamine sulfate, disodium hydrogen phosphate, potassium hydrogen phosphate, sodium chloride, zinc salt, colloidal silica, magnesium trisilicate, polyvinylpyrrolidone, cellulose, polyethylene glycol, sodium carboxymethylcellulose, polyacrylate, beeswax, lanolin, and the like. The amount of the carrier in the pharmaceutical composition may be 1% to 98% by weight, usually about 80% by weight. For the convenience, topical anesthetic, antiseptic, buffer and etc. may be directly dissolved in the carrier.

Oral tablets and capsules may comprise excipients e.g., binders such as syrup, Arabic gum, sorbitol, tragacanth, or polyvinylpyrrolidone, fillers such as lactose, sucrose, corn starch, calcium phosphate, sorbitol, aminoacetic acid, lubricant such as magnesium stearate, saponite, polyethylene glycol, silica, disintegrating agent such as potato starch, or acceptable moisturizing agent such as sodium lauryl sulfate. Tablets may be coated by using known methods in pharmaceutics.

Oral solution may be made as a suspension of water and oil, a solution, an emulsion, a syrup or an elixir, or made as a dried product to which water or other medium is added before use. This liquid preparation may comprise conventional additives, e.g., suspending agent such as sorbitol, cellulose methyl ether, glucose syrup, gelatin, hydroxyethyl cellulose, carboxymethyl cellulose, aluminum stearate gel, hydrogenated edible grease; emulsifying agent such as lecithin, sorbitan monooleate, Arabic gum; or non-aqueous carrier (possibly including edible oil), such as almond oil, grease such as glycerin, ethylene glycol, or ethanol; antiseptic such as methyl or propyl p-hydroxybenzoate, sorbic acid. If desired, a flavoring agent or a colorant may be added.

Suppository may comprise a conventional suppository substrate, such as cocoa butter or other glyceride.

For non-gastric administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an enclosed bottle or ampoule.

For topical application on skin, the compound of the present invention may be made into a suitable form of ointment, lotion or cream, wherein the active ingredient is suspended or dissolved in one or more carrier(s). The carrier used for an ointment includes, but not limited to, mineral oil, liquid vaseline, white vaseline, propylene glycol, polyoxyethylene, polyoxypropylene, emulsified wax and water; the carrier used for a lotion and a cream includes, but not limited to, mineral oil, sorbitan monostearic ester, Tween 60, cetyl esters wax, hexadecylene aromatic alcohol, 2-octyl dodecanol, benzanol and water.

In the above preparations, the active compound of formula (I) exists in a concentration of about 0.1 to 99.5% by weight, preferably about 0.5 to 95% by weight, based on the total weight of the mixture.

The above preparations may further comprise other pharmaceutically active compounds, in addition to the compound of formula (I).

In general, it has been proved that, advantageously, whether in human medicine or in veterinary medicine, the total dose of the active compound of the present invention is about 0.5 to 500 mg every 24 hr, preferably 1 to 100 mg per kg body weight. If appropriate, the drug is administrated by single dose for multiple times, to thereby achieve the desired effect. The amount of the active compound in a single dose is preferably about 1 to 80 mg, more preferably 1 to 50 mg per kg weight body. Nevertheless, the dose may also be varied according to the type and body weight of the object to be treated, the kind and extent of severity of diseases, the type of the preparation and the administration manner of the drug, and the administration period or the time interval.

CONCRETE MODES FOR CARRYING OUT THE INVENTION

The following examples are preferred embodiments of the present invention, and shall not be understood to limit the present invention in any manner.

The melting point of the compound was determined by using RY-1 melting point apparatus, and the thermometer was not calibrated. Mass spectrum was determined by using Micromass ZabSpec high resolution mass spectrograph (resolution 1000). ¹H NMR was determined by using JNM-ECA-400 superconductive NMR spectrometer, the working frequency being ¹H NMR 400 MHz, ¹³C NMR 100 MHz.

EXAMPLES

Example 1

Preparation of ethyl 2-(thiazol-4-yl)-4-(2-chloro-4-fluorophenyl)-6-methyl-1,4-dihydro-pyrimidin-5-carboxylate

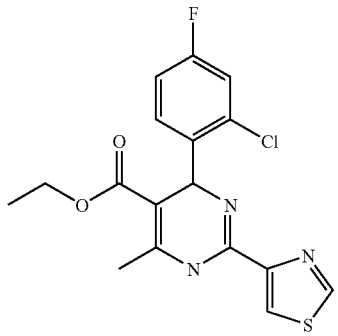

2 mmol 4-Thiazolyl formamidine (Diana, G. D., Yarinsky, A., Zalay, E. S., et al. J. Med. Chem. 1969, 12(9):791-793), 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.28 g of a yellow crystal (yield 37%) with mp 140-142° C.; ¹H-NMR (400 MHz, DMSO-d₆) δ 1.01-1.05 (3H, m); 2.49 (3H, s); 3.92-3.95 (2H, m); 5.99 (1H, s); 7.36-7.39 (3H, m); 8.15 (1H, d, J=1.96 Hz); 9.18 (1H, d, J=1.96 Hz); 9.47 (1H, s); MS (FAB) 380.2 (M+1).

Example 2

Preparation of ethyl 2-(thiazol-4-yl)-4-(3-fluorophenyl)-6-methyl-1,4-dihydro-pyrimidin-5-carboxylate

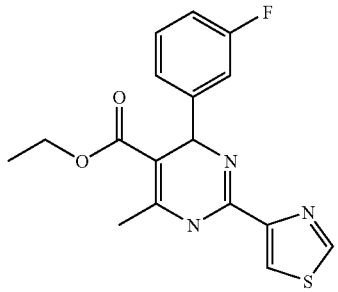

Using the method of Example 1, while using 3-fluorobenzaldehyde in place of 2-chloro-4-fluorobenzaldehyde, 0.22 g of yellowish granulates were obtained (yield 32%), with mp 118-120° C.; ¹H-NMR (400 MHz, DMSO-d₆) δ 1.11-1.15 (3H, m); 2.49 (3H, s); 4.03-4.05 (2H, m); 5.63 (1H, br); 7.02-7.34 (4H, m); 8.31 (1H.br); 9.21 (1H, d); 9.54 (1H, br); MS (FAB) 346.3 (M+1).

Example 3

Preparation of ethyl 2-(thiazol-4-yl)-4-(4-fluorophenyl)-6-methyl-1,4-dihydro-pyrimidin-5-carboxylate

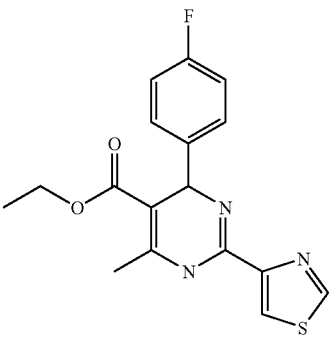

Using the method of Example 1, while using 4-fluorobenzaldehyde in place of 2-chloro-4-fluorobenzaldehyde, 0.27 g of a yellowish crystal was obtained (yield 39%), with mp 118-120° C.; ¹H-NMR (400 MHz, DMSO-d₆) δ 1.11-1.15 (3H, m); 2.49 (3H, s); 4.01-4.03 (2H, m); 5.59 (1H, d, J=3.36); 7.11-7.31 (4H, m); 8.25-8.40 (1H, d, J=1.96); 9.21-9.22 (1H, d, J=1.96); 9.35-9.50 (1H, d, J=3.36); MS (FAB) 346.2 (M+1).

Example 4

Preparation of ethyl 2-(thiazol-4-yl)-4-(3-methylphenyl)-6-methyl-1,4-dihydro-pyrimidin-5-carboxylate

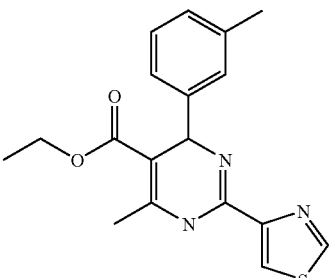

Using the method of Example 1, while using 3-methylbenzaldehyde in place of 2-chloro-4-fluorobenzaldehyde, 0.24 g of a yellow blocky crystal was obtained (yield 35%), with mp 133-134° C.; ¹H-NMR (400 MHz, DMSO-d₆) δ 1.11-1.15 (3H, m); 2.25 (3H, s); 2.49 (3H, s); 4.00-4.02 (2H, m); 5.47-

5.55 (1H, br); 7.01-7.17 (4H, m); 8.24-8.39 (1H, br); 9.20 (1H, d); 9.40 (1H, br); MS (FAB) 342.1 (M+1).

Example 5

Preparation of Ethyl 2-(thiazol-4-yl)-4-(4-methylphenyl)-6-methyl-1,4-dihydro-pyrimidin-5-carboxylate

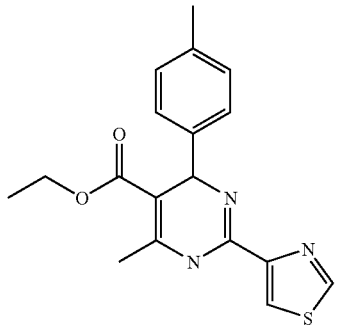

Using the method of Example 1, while using 4-methylbenzaldehyde in place of 2-chloro-4-fluorobenzaldehyde, 0.22 g of an amorphous solid was obtained (yield 33%); with $^1$H-NMR (400 MHz, DMSO-$d_6$) δ 1.11-1.15 (3H, m); 2.24 (3H, s); 2.38-2.49 (3H, br); 4.00-4.04 (2H, m); 5.44-5.54 (1H, br); 7.1-7.17 (4H, m); 8.23-8.37 (1H, br); 9.20 (1H, s); 9.25-9.41 (1H, br); MS (FAB) 342.1 (M+1).

Example 6

Preparation of ethyl 2-(thiazol-4-yl)-4-(3-methoxyphenyl)-6-methyl-1,4-dihydro-pyrimidin-5-carboxylate

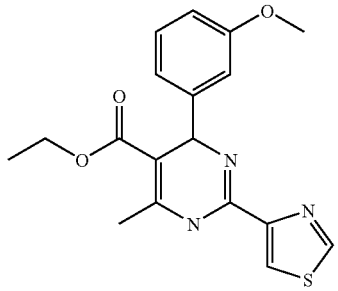

Using the method of Example 1, while using 3-methoxybenzaldehyde in place of 2-chloro-4-fluorobenzaldehyde, 0.26 g of yellow granulates were obtained (yield 36%), with mp 140-142° C.; $^1$H-NMR (400 MHz, DMSO-$d_6$) δ 1.13-1.15 (3H, m); 2.35-2.49 (3H, d); 3.70 (3H, s); 4.01-4.03 (2H, m); 5.46-5.58 (1H, ds, J=3.36); 6.81-6.87 (3H, m); 7.20-7.22 (1H, m); 8.26-8.39 (1H, dd, J=1.96); 9.21-9.22 (1H, dd, J=1.96); 9.30-9.47 (1H, ds, J=3.36); MS (FAB) 358.2 (M+1).

Example 7

Preparation of ethyl 1-acetyl-2-(thiazol-4-yl)-4-(3-methoxyphenyl)-6-methyl-1,4-dihydro-pyrimidin-5-carboxylate

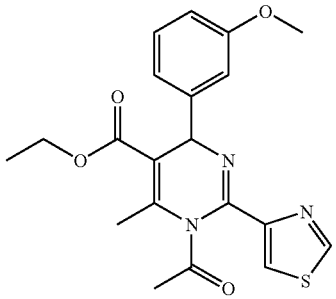

0.25 g of Ethyl 2-(thiazol-4-yl)-4-(3-methoxyphenyl)-6-methyl-1,4-dihydro-pyrimidin-5-carboxylate (Example 6) was reacted with acetic anhydride under reflux for 1 hr, and then the resultant product was extracted with ethyl acetate, dried, and then separated by a column chromatography to obtain 0.21 g of a yellowish fine needle crystal (yield 75%), with mp 130-131° C.; $^1$H-NMR (400 MHz, CDCl$_3$) δ 1.26-1.29 (3H, t); 1.97 (3H, s); 2.58 (3H, s); 3.73 (3H, s); 4.23-4.24 (2H, m); 6.63 (1H, s); 6.73-6.75 (1H, m); 6.91-6.96 (2H, m); 7.13-7.17 (1H, t); 8.0 (1H, s); 8.81-8.82 (1H, d); MS (FAB) 400.1 (M+1).

Example 8

Preparation of ethyl 2-(thiazol-4-yl)-4-(4-methoxyphenyl)-6-methyl-1,4-dihydro-pyrimidin-5-carboxylate

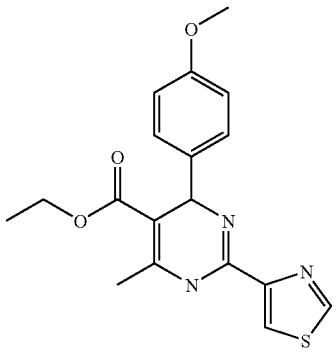

Using the method of Example 1, while using 4-methoxybenzaldehyde in place of 2-chloro-4-fluorobenzaldehyde, 0.15 g of an amorphous solid was obtained (yield 20%); with $^1$H-NMR (400 MHz, DMSO-$d_6$) δ 1.12-1.15 (3H, m); 2.38 (3H, s); 3.70 (3H, s); 4.01-4.04 (2H, m); 5.43-5.53 (1H, br);

6.84-6.86 (2H, m); 7.19-7.21 (2H, m); 8.23-8.37 (1H, br); 9.20-9.41 (2H, br); MS (FAB) 358.2 (M+1).

Example 9

Preparation of ethyl 2-(thiazol-4-yl)-4-(3-hydroxyphenyl)-6-methyl-1,4-dihydro-pyrimidin-5-carboxylate

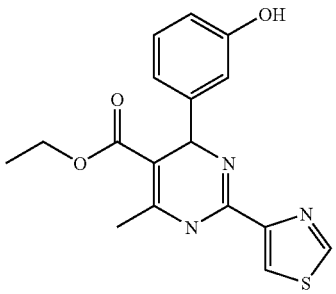

Using the method of Example 1, while using 3-hydroxybenzaldehyde in place of 2-chloro-4-fluorobenzaldehyde, 0.21 g of yellow granulates were obtained (yield 30%), with mp 180-183° C.; $^1$H-NMR (400 MHz, DMSO-d$_6$) δ 1.14-1.17 (3H, m); 2.34-2.38 (3H, d); 4.02-4.04 (2H, m); 5.41-5.52 (1H, m); 6.56-6.61 (1H, m); 6.70-6.73 (2H, m); 7.05-7.07 (1H, m); 8.24-8.38 (1H, m); 9.20-9.42 (3H, m); MS (FAB) 343.9 (M+1).

Example 10

Preparation of ethyl 2-(thiazol-4-yl)-4-(4-hydroxyphenyl)-6-methyl-1,4-dihydro-pyrimidin-5-carboxylate

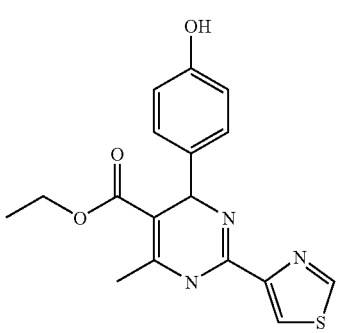

Using the method of Example 1, while using 4-hydroxybenzaldehyde in place of 2-chloro-4-fluorobenzaldehyde, 0.25 g of yellow granulates were obtained, with mp 213-216° C.; $^1$H-NMR (400 MHz, DMSO-d$_6$) δ 1.12-1.15 (3H, m); 2.34-2.38 (3H, d); 3.99-4.02 (2H, m); 5.37-5.47 (1H, m); 6.64-6.67 (2H, m); 7.06-7.09 (2H, m); 8.22-8.37 (1H, m); 9.19-9.36 (3H, m); MS (FAB) 344.1 (M+1).

Example 11

Preparation of ethyl 2-(thiazol-4-yl)-4-(3-chlorophenyl)-6-methyl-1,4-dihydro-pyrimidin-5-carboxylate

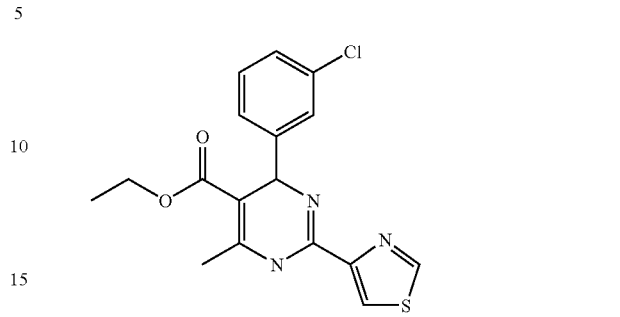

Using the method of Example 1, while using 3-chlorobenzaldehyde in place of 2-chloro-4-fluorobenzaldehyde, 0.27 g of a yellow solid was obtained, with mp 105-108° C.; $^1$H-NMR (400 MHz, DMSO-d$_6$) δ 1.12-1.15 (3H, m); 2.36-2.40 (3H, s); 4.02-4.05 (2H, m); 5.61 (1H, br); 7.27-7.29 (4H, m); 8.29 (1H, br); 9.22 (1H, s); 9.36-9.56 (1H, br); MS (FAB) 361.9 (M+1).

Example 12

Preparation of ethyl 2-(thiazol-4-yl)-4-(2-fluorophenyl)-6-methyl-1,4-dihydro-pyrimidin-5-carboxylate

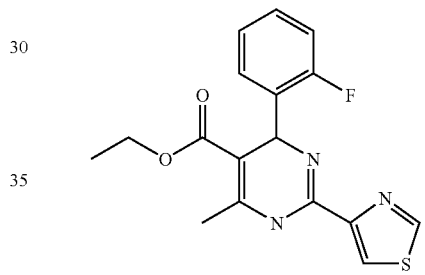

Using the method of Example 1, while using 2-fluorobenzaldehyde in place of 2-chloro-4-fluorobenzaldehyde, 0.26 g of yellow granulates were obtained, with mp 126-128° C.; $^1$H-NMR (400 MHz, DMSO-d$_6$) δ 1.04-1.08 (3H, m); 2.42 (3H, br); 3.94-3.96 (2H, m); 5.89 (1H, br); 7.11-7.15 (4H, m); 8.20 (1H, br); 9.19 (1H, d); 9.44 (1H, br); MS (FAB) 346.1 (M+1).

Example 13

Preparation of ethyl 2-(thiazol-4-yl)-4-(4-chlorophenyl)-6-methyl-1,4-dihydro-pyrimidin-5-carboxylate

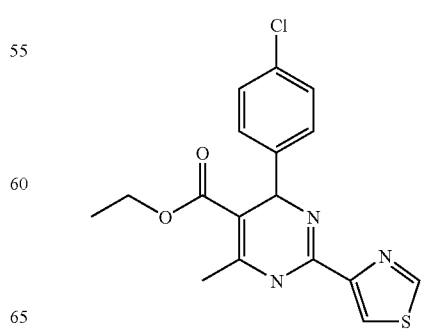

Using the method of Example 1, while using 4-chlorobenzaldehyde in place of 2-chloro-4-fluorobenzaldehyde, 0.30 g of an amorphous solid was obtained; with H-NMR (400 MHz, DMSO-$d_6$) δ 1.11-1.15 (3H, m); 2.36-2.39 (3H, d); 3.99-4.04 (2H, m); 5.45-5.60 (1H, d); 7.28-7.38 (4H, m); 8.26-8.40 (1H, d); 9.21 (1H, s); 9.36-9.52 (1H, d); MS (FAB) 361.9 (M+1).

Example 14

Preparation of ethyl 2-(thiazol-4-yl)-4-phenyl-6-methyl-1,4-dihydro-pyrimidin-5-carboxylate

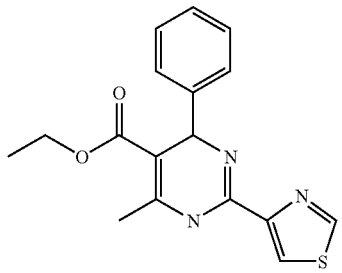

Using the method of Example 1, while using benzaldehyde in place of 2-chloro-4-fluorobenzaldehyde, 0.24 g of an amorphous solid was obtained; with $^1$H-NMR (400 MHz, DMSO-$d_6$) δ 1.11-1.15 (3H, m); 2.38 (3H, d); 4.01-4.03 (2H, m); 5.57 (1H, br); 7.19-7.39 (5H, m); 8.28 (1H, br); 9.21 (1H, s); 9.31-9.45 (1H, br); MS (FAB) 361.9 (M+1).

Example 15

Preparation of ethyl 2-(2-methylthiazol-4-yl)-4-(2-chloro-4-fluorophenyl)-6-methyl-1,4-dihydro-pyrimidin-5-carboxylate

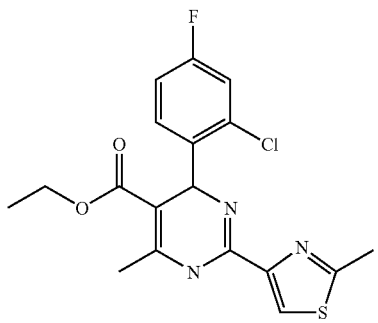

2 mmol 2-Methylthiazolyl-4-formamidine (Diana, G. D., Yarinsky, A., Zalay, E. S., et al. J. Med. Chem. 1969, 12(9): 791-793), 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.28 g of a yellow crystal with mp 123-125° C.; $^1$H-NMR (400 MHz, DMSO-$d_6$) δ 1.01-1.05 (3H, m); 2.37-2.43 (3H, d); 2.66-2.69 (3H, d); 3.92-3.95 (2H, m); 5.89-5.97 (1H, m); 7.14-7.19 (1H, m); 7.33-7.39 (2H, m); 7.91-8.18 (1H, d); 8.91-9.27 (1H, d); MS (FAB) 394.1 (M+1).

Example 16

Preparation of ethyl 2-(2-methylthiazol-4-yl)-4-(3-hydroxyphenyl)-6-methyl-1,4-dihydro-pyrimidin-5-carboxylate

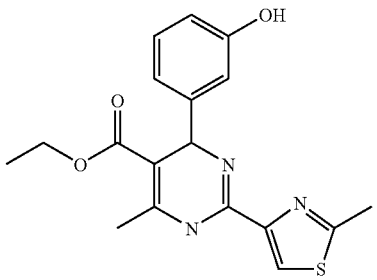

Using the method of Example 15, while using 3-hydroxybenzaldehyde in place of 2-chloro-4-fluorobenzaldehyde, 0.24 g of a colorless crystal was obtained, with mp 175-178° C.; $^1$H-NMR (400 MHz, DMSO-$d_6$) δ 1.13-1.17 (3H, m); 2.33-2.37 (3H, d); 2.69-2.72 (3H, d); 4.00-4.03 (2H, m); 5.34-5.50 (1H, m); 6.56-6.61 (1H, m); 6.68-6.72 (2H, m); 7.03-7.09 (1H, m); 8.01-8.16 (1H, d); 9.09-9.32 (2H, m); MS (FAB) 358.2 (M+1).

Example 17

Preparation of ethyl 2-(2-methylthiazol-4-yl)-4-(4-hydroxyphenyl)-6-methyl-1,4-dihydro-pyrimidin-5-carboxylate

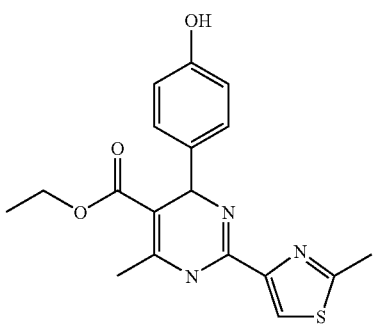

Using the method of Example 15, while using 4-hydroxybenzaldehyde in place of 2-chloro-4-fluorobenzaldehyde, 0.29 g of a yellow columnar crystal was obtained, with mp 208-210° C.; $^1$H-NMR (400 MHz, DMSO-$d_6$) δ 1.12-1.16 (3H, m); 2.33-2.36 (3H, d); 2.68-2.71 (3H, d); 3.99-4.02 (2H, m); 5.34-5.45 (1H, d, br); 6.65-6.67 (2H, m); 7.05-7.07 (2H, m); 8.0-8.14 (1H, d, br); 9.05-9.33 (2H, m); MS (FAB) 358.2 (M+1).

Example 18

Preparation of ethyl 2-(2-methylthiazol-4-yl)-4-(3-chlorophenyl)-6-methyl-1,4-dihydro-pyrimidin-5-carboxylate

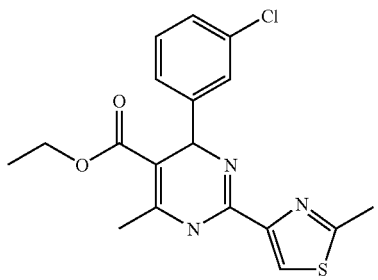

Using the method of Example 15, while using 3-chlorobenzaldehyde in place of 2-chloro-4-fluorobenzaldehyde, 0.23 g of a colorless needle crystal were obtained, with mp 143-144° C.; $^1$H-NMR (400 MHz, DMSO-d$_6$) δ 1.11-1.14 (3H, m); 2.36-2.39 (3H, d); 2.69-2.72 (3H, d); 4.01-4.05 (2H, m); 5.46-5.59 (1H, d); 7.23-7.36 (4H, m); 8.04-8.19 (1H, d); 9.26-9.41 (1H, m); MS (FAB) 376.2 (M+1).

Example 19

Preparation of ethyl 1-acetyl-2-(2-methylthiazol-4-yl)-4-(3-fluorophenyl)-6-methyl-1,4-dihydro-pyrimidin-5-carboxylate

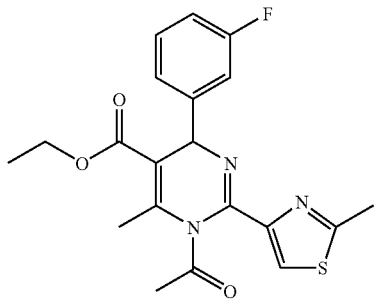

Using the method of Example 15, while using 3-fluorobenzaldehyde in place of 2-chloro-4-fluorobenzaldehyde, an oily substance was obtained; and then, the oily substance was further reacted Using the method of Example 7, to thereby obtain 0.18 g of a yellow crystal, with mp 127-130° C.; $^1$H-NMR (400 MHz, DMSO-d$_6$) δ 1.20-1.23 (3H, t); 1.90 (3H, s); 2.46 (3H, d); 2.68 (3H, s); 4.20-4.23 (2H, m); 6.45 (1H, s); 7.04-7.11 (3H, m); 7.32-7.37 (1H, m); 8.25 (1H, s); MS (FAB) 402.1 (M+1).

Example 20

Preparation of ethyl 1-acetyl-2-(2-methylthiazol-4-yl)-4-(4-fluorophenyl)-6-methyl-1,4-dihydro-pyrimidin-5-carboxylate

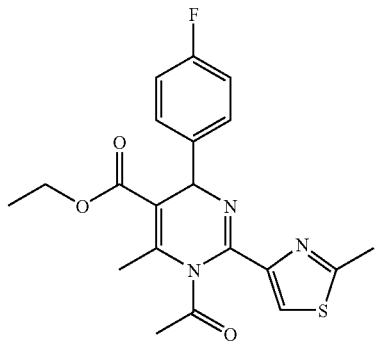

Using the method of Example 19, while using 4-fluorobenzaldehyde in place of 3-fluorobenzaldehyde, 0.20 g of a yellow crystal was obtained, with mp 140-142° C.; $^1$H-NMR (400 MHz, DMSO-d$_6$) δ 1.18-1.22 (3H, t); 1.88 (3H, s); 2.46 (3H, s); 2.66 (3H, s); 4.17-4.20 (2H, m); 6.43 (1H, s); 7.10-7.15 (2H, m); 7.25-7.29 (2H, m); 8.22 (1H, s); MS (FAB) 402.0 (M+1).

Example 21

Preparation of ethyl 1-acetyl-2-(2-methylthiazol-4-yl)-4-(3-methylphenyl)-6-methyl-1,4-dihydro-pyrimidin-5-carboxylate

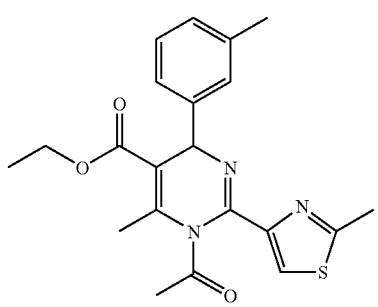

Using the method of Example 19, while using 3-methylbenzaldehyde in place of 3-fluorobenzaldehyde, 0.17 g of a yellow blocky crystal was obtained, with mp 113-114° C.; $^1$H-NMR (400 MHz, CDCl$_3$) δ 1.23-1.27 (3H, t); 1.97 (3H, s); 2.26 (3H, s); 2.61 (3H, s); 2.73 (3H, s); 4.17-4.24 (2H, m); 6.63 (1H, s); 7.01-7.03 (1H, m); 7.12-7.14 (3H, m); 7.48 (1H, br); MS (FAB) 398.1 (M+1).

Example 22

Preparation of ethyl 1-acetyl-2-(2-methylthiazol-4-yl)-4-(4-methylphenyl)-6-methyl-1,4-dihydro-pyrimidin-5-carboxylate

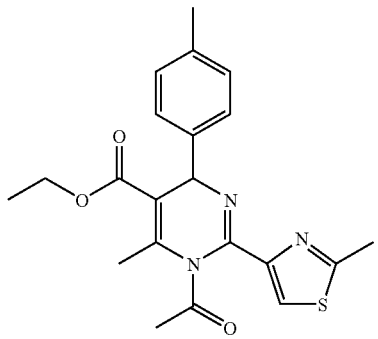

Using the method of Example 19, while using 4-methylbenzaldehyde in place of 3-fluorobenzaldehyde, 0.21 g of a yellow prismy crystal was obtained, with mp 187-188° C.; $^1$H-NMR (400 MHz, DMSO-$d_6$) δ 1.18-1.21 (3H, t); 1.89 (3H, s); 2.21 (3H, s); 2.44 (3H, s); 2.66 (3H, s); 4.15-4.18 (2H, m); 6.42 (1H, s 7.06-7.13 (4H, m); 8.18 (1H, s); MS (FAB) 398.1 (M+1).

Example 23

Preparation of ethyl 1-acetyl-2-(2-methylthiazol-4-yl)-4-(3-methoxyphenyl)-6-methyl-1,4-dihydro-pyrimidin-5-carboxylate

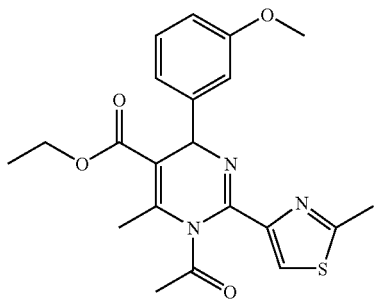

Using the method of Example 19, while using 3-methoxybenzaldehyde in place of 3-fluorobenzaldehyde, 0.18 g of a yellow prismy crystal was obtained, with mp 114-116° C.; $^1$H-NMR (400 MHz, CDCl$_3$) δ 1.25-1.28 (3H, t); 1.98 (3H, s); 2.60 (3H, s); 2.72 (3H, s); 3.74 (3H, s); 4.22-4.24 (2H, m); 6.63 (1H, s); 6.73-6.76 (1H, q); 6.88-6.90 (1H, d); 6.94-6.95 (1H, d); 7.13-7.16 (1H, t); 7.63 (1H, br); MS (FAB) 414.2 (M+1).

Example 24

Preparation of ethyl 1-acetyl-2-(2-methylthiazol-4-yl)-4-(4-methoxyphenyl)-6-methyl-1,4-dihydro-pyrimidin-5-carboxylate

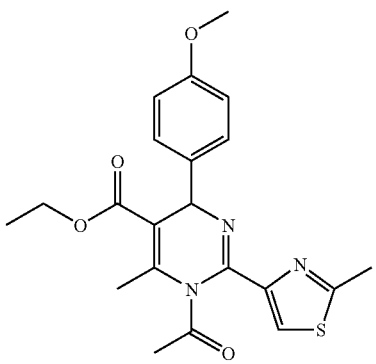

Using the method of Example 19, while using 4-methoxybenzaldehyde in place of 3-fluorobenzaldehyde, 0.17 g of a yellow columnar crystal was obtained, with mp 138-140° C.; $^1$H-NMR (400 MHz, CDCl$_3$) δ 1.22-1.25 (3H, t); 1.95 (3H, s); 2.60 (3H, s); 2.72 (3H, s); 3.74 (3H, s); 4.16-4.19 (2H, m); 6.60 (1H, s); 6.74-6.77 (2H, m); 7.24-7.26 (2H, m); 7.42 (1H, br); MS (FAB) 414.1 (M+1).

Example 25

Preparation of ethyl 1-acetyl-2-(2-methylthiazol-4-yl)-4-phenyl-6-methyl-1,4-dihydro-pyrimidin-5-carboxylate

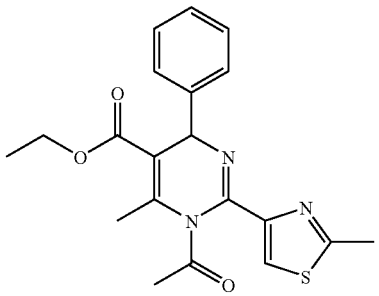

Using the method of Example 19, while using benzaldehyde in place of 3-fluorobenzaldehyde, 0.20 g of a yellow columnar crystal was obtained, with mp 140-142° C.; $^1$H-NMR (400 MHz, DMSO-$d_6$) δ 1.19-1.22 (3H, t); 1.89 (3H, s); 2.45 (3H, s); 2.67 (3H, s); 4.18-4.20 (2H, m); 6.46 (1H, s); 7.21-7.30 (5H, m); 8.21 (1H, s); MS (FAB) 384.1 (M+1).

Example 26

Preparation of ethyl 1-acetyl-2-(2-methylthiazol-4-yl)-4-(4-chlorophenyl)-6-methyl-1,4-dihydro-pyrimidin-5-carboxylate

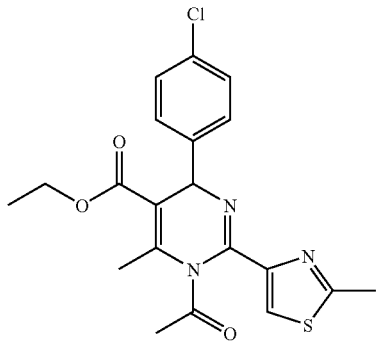

Using the method of Example 19, while using 4-chlorobenzaldehyde in place of 3-fluorobenzaldehyde, 0.19 g of a yellow prismy crystal was obtained, with mp 169-171° C.; $^{1}$H-NMR (400 MHz, CDCl$_3$) δ 1.23-1.26 (3H, t); 1.96 (3H, s); 2.60 (3H, s); 2.72 (3H, s); 4.17-4.23 (2H, m); 6.60 (1H, s); 7.20-7.29 (4H, m); MS (FAB) 418.0 (M+1).

Example 27

Preparation of ethyl 1-acetyl-2-(2-methylthiazol-4-yl)-4-(2-chloro-1-fluorophenyl)-6-methyl-1,4-dihydro-pyrimidin-5-carboxylate

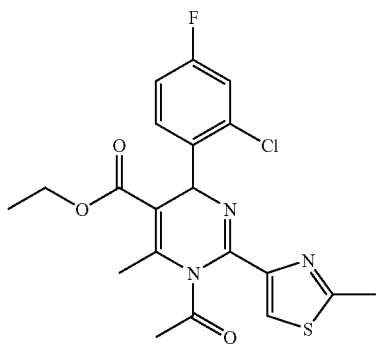

Using the method of Example 19, while using 2-chloro-4-fluorobenzaldehyde in place of 3-fluorobenzaldehyde, 0.18 g of a yellow fine needle crystal was obtained, with mp 164-166° C.; $^{1}$H-NMR (400 MHz, DMSO-d$_6$) δ 1.14-1.18 (3H, t); 1.85 (3H, s); 2.48 (3H, s); 2.62 (3H, s); 4.08-4.13 (2H, m); 6.83 (1H, s); 7.07-7.09 (2H, m); 7.44-7.46 (1H, m); 8.09 (1H, s).

Example 28

Preparation of methyl 2-(thiazol-4-yl)-4-(2-chloro-4-fluorophenyl)-6-ethyl-1,4-dihydro-pyrimidin-5-carboxylate

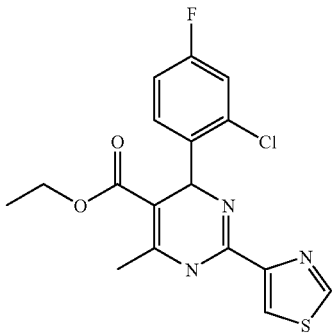

Using the method of Example 1, while using methyl acetoacetate in place of ethyl acetoacetate, 0.28 g of a yellow blocky crystal was obtained, with mp 144-147° C.; $^{1}$H-NMR (400 MHz, DMSO-d$_6$) δ 2.39-2.46 (3H, d); 3.49-3.51 (3H, d); 5.98 (1H, s); 7.17-7.20 (1H, m); 7.33-7.40 (2H, m); 8.16 (1H, s); 9.19 (1H, s); 9.55 (1H, s); MS (EI) 365.1 (M$^+$).

Example 29

Preparation of methyl 2-(2-methylthiazol-4-yl)-4-(2-chloro-4-fluorophenyl)-6-methyl-1,4-dihydro-pyrimidin-5-carboxylate

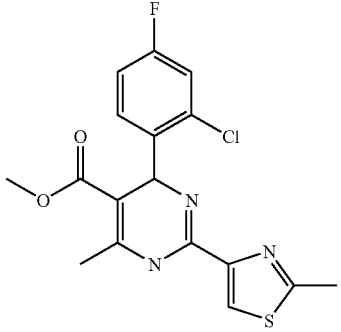

Using the method of Example 15, while using methyl acetoacetate in place of ethyl acetoacetate, 0.25 g of a yellowish crystal was obtained, with mp 128-130° C.; $^{1}$H-NMR (400 MHz, DMSO-d$_6$) δ 2.37-2.45 (3H, d); 2.67-2.70 (3H, d); 3.48-3.50 (3H, d); 5.88-5.96 (1H, m); 7.14-7.39 (3H, m); 7.14-7.19 (1H, m); 7.92-8.19 (1H, d); 9.0-9.4 (1H, d); MS (EI) 393.1 (M$^+$).

Example 30

Preparation of ethyl 2-(2-acetylaminothiazol-4-yl)-4-(2-chloro-1-fluorophenyl)-6-methyl-1,4-dihydro-pyrimidin-5-carboxylate

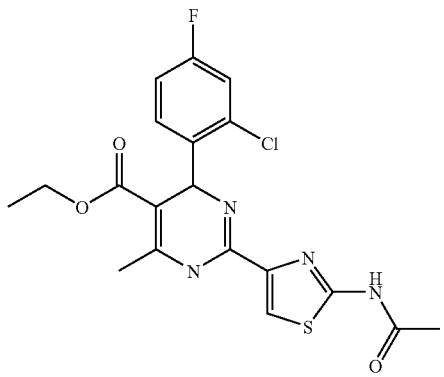

Step 1 Preparation of ethyl 2-aminothiazol-4-carboxylate 7.8 g (40 mmol) ethyl bromopyruvate and 3.1 g (40 mmol) thiourea were dissolved in 40 ml ethanol, and reacted at room temperature, to precipitate a white solid, which was filtered, washed and dried to obtain 7.5 g ethyl 2-aminothiazol-4-carboxylate (yield 74%) with mp 177-181° C.

Step 2 Preparation of 2-aminothiazol-4-carboxamide 3.0 g Ethyl 2-aminothiazol-4-carboxylate was added to 100 ml ammonia water, reacted for 2 hr, concentrated, and placed aside to precipitate a needle crystal, which was filtered, washed with water, and dried to obtain 1.9 g 2-aminothiazol-4-carboxamide (yield 76%) with mp 208-211° C.

Step 3 Preparation of 2-acetylaminothiazol-4-carboxamide 4. g (28 mmol) 2-Aminothiazol-4-carboxamide was dissolved in 40 ml glacial acetic acid, to which added 2.8 ml (29.6 mmol) acetic anhydride, followed by reacting under reflux for 2 hr, and naturally cooling down to precipitate a large quantity of solids, which were filtered, washed and dried to obtain 4.7 g 2-acetylaminothiazol-4-carboxamide (yield 92%) with mp>250° C.

Step 4 Preparation of 2-acetylamino-4-cyanothiazole 5.1 g (27.5 mmol) 2-Acetylaminothiazol-4-carboxamide was dispersed in 27 ml pyridine, and 10.5 g (55 mmol) p-tolylsulfonyl chloride was added, to carry out reaction at room temperature for 10 hr, and then 150 ml ethyl acetate and 100 ml water were added to separate the layers. The resultant organic phase was washed with diluted HCl till aqueous phase being acidic, and then washed with saturated sodium chloride, dried over anhydrous sodium sulfate, filtered, and concentrated to obtain 3.45 g 2-acetylamino-4-cyanothiazole (yield 75%) with mp 185-188° C. (ethyl acetate). $^1$H NMR (DMSO-$d_6$) 2.18 (3H, s); 8.33 (1H, s); 12.55 (1H, s).

Step 5 Preparation of 2-acetylamino-4-thiazolformamidine hydrochloride 10 mmol 2-Acetylamino-4-cyanothiazole was dissolved in 10 ml anhydrous methanol, and 10 mmol sodium methoxide was added. Upon complete reaction of the starting materials, 20 mmol ammonium chloride was added, to carry out reaction in closed state for 12 hr. The reaction product was filtered to remove inorganic salt, and then the resultant filtrate was concentrated to obtain 2-acetylamino-4-thiazolformamidine hydrochloride.

Step 6 Preparation of ethyl 2-(2-acetylaminothiazol-4-yl)-4-(2-chloro-4-fluorophenyl)-6-methyl-1,4-dihydro-pyrimidin-5-carboxylate 2 mmol 2-Acetylamino-4-thiazolformamidine hydrochloride, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.31 g of a colorless crystal with mp 220-223° C.; $^1$H-NMR (400 MHz, DMSO-$d_6$) δ 1.01-1.04 (3H, m); 2.13 (3H, s); 2.40-2.42 (3H, d); 3.91-3.97 (2H, m); 5.97 (1H, s); 7.15-7.39 (3H, m); 7.64-7.83 (1H, d); 8.33-8.98 (1H, d); 12.33 (1H, s); MS (EI) 436.0 (M$^+$).

Example 31

Preparation of ethyl 2-(2-aminothiazol-4-yl)-4-(2-chloro-4-fluorophenyl)-6-methyl-1,4-dihydro-pyrimidin-5-carboxylate

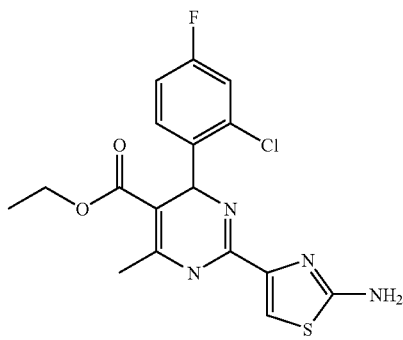

0.35 g Ethyl 2-(2-acetylaminothiazol-4-yl)-4-(2-chloro-4-fluorophenyl)-6-methyl-1,4-dihydro-pyrimidin-5-carboxylate (Example 30) reacted with 2 ml 6 mol/L hydrochloric acid solution at 50° C. for 2 hr. The reaction product was extracted with ethyl acetate, dried, and separated by a column chromatography to obtain 0.25 g of amorphous yellow solid with mp 95-110° C.; $^1$H-NMR (400 MHz, DMSO-$d_6$) δ 1.01-

1.04 (3H, m); 2.39 (3H, s); 3.89-3.95 (2H, m); 5.91 (1H, br); 7.02-7.38 (6H, m, br); 8.83 (1H, br); MS (EI) 394.0 (M+).

Example 32

Preparation of ethyl 2-(5-chlorothiazol-4-yl)-4-(2-chloro-4-fluorophenyl)-6-methyl-1,4-dihydro-pyrimidin-5-carboxylate

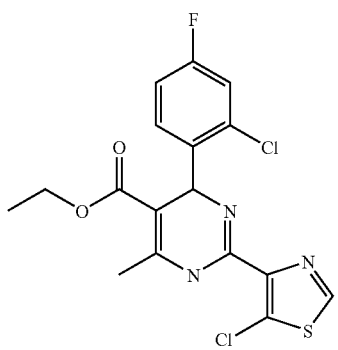

Step 1 Preparation of ethyl 5-chlorothiazol-4-carboxylate 21 g (123 mmol) ethyl 2-aminothiazol-4-carboxylate (Example 30, step 1) was added to 150 ml acetonitrile, and 18.4 g (137 mmol) NCS was added portionwise, to carry out reaction at room temperature overnight; and then, 19 ml (137 mmol) isoamyl nitrite was added rapidly dropwise, followed by continuing the reaction for 2 hr after complete of addition. The resultant reaction mixture was concentrated, then ethyl acetate and water were added, and filtered to remove insoluble solids. The organic phase was dried over anhydrous sodium sulfate, filtered, and concentrated to obtain 20 g ethyl 5-chlorothiazol-4-carboxylate $^1$H NMR (CDCl$_3$) 1.42-1.45 (3H, t, J=7.0 Hz); 4.43-4.46 (2H, m, J=7.0 Hz); 8.68 (1H, s); MS (EI) 191.0 (M+).

Step 2 Preparation of 5-chlorothiazol-4-carboxamide 20 g Ethyl 5-chlorothiazol-4-carboxylate was added to 150 ml ammonia water, and reacted at room temperature with stirring for 5 hr. The resultant reaction mixture was extracted with ethyl acetate, dried over anhydrous sodium sulfate, filtered and concentrated to obtain 9.5 g of a crude product which was recrystallized from ethyl acetate to obtain 5.8 g of a needle crystal (yield 30%) with mp 213-216° C.; $^1$H NMR (DMSO-d$_6$) 7.69 (1H, s); 7.83 (1H, s); 9.05 (1H, s).

Step 3 Preparation of 4-cyano-5-chlorothiazole 5.8 g (35.7 mmol) 5-chlorothiazol-4-carboxamide was dissolved in 35 ml pyridine, and 13.6 g (71.4 mmol) p-tolylsulfonyl chloride was added, to carry out reaction overnight; and then, ethyl acetate and water were added to separate the layers. The resultant organic phase was washed with diluted HCl till aqueous phase being acidic, and then washed with saturated sodium chloride, dried over anhydrous sodium sulfate, filtered, concentrated and separated by a column chromatography to obtain 3.1 g 5-chloro-4-cyanothiazole (yield 60%), which was placed aside to precipitate a needle crystal with mp 36-39° C., $^{13}$C NMR (CDCl$_3$, ppm) 111.72, 126.65, 138.96, 152.55.

Step 4 Preparation of 5-chloro-4-thiazolformamidine hydrochloride 10 mmol 5-chloro-4-cyanothiazole was dissolved in 10 ml anhydrous methanol, and 10 mmol sodium methoxide was added. Upon complete reaction of the starting materials, 20 mmol ammonium chloride was added, to carry out reaction in closed state for 12 hr. The reaction product was filtered to remove inorganic salt, and then the resultant filtrate was concentrated to obtain 5-chloro-4-thiazolformamidine hydrochloride.

Step 5 Preparation of ethyl 2-(5-chlorothiazol-4-yl)-4-(2-chloro-4-fluorophenyl)-6-methyl-1,4-dihydro-pyrimidin-5-carboxylate 2 mmol 5-chloro-4-thiazolformamidine hydrochloride, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.29 g of a yellowish solid with mp 149-152° C.; $^1$H-NMR (400 MHz, DMSO-d$_6$) δ 1.02-1.06 (3H, m); 2.42 (3H, s); 3.92-3.97 (2H, m); 6.01 (1H, br); 7.16-7.41 (3H, m); 9.08 (1H, s); 9.58 (1H, s); MS (EI) 413.1 (M+).

Example 33

Preparation of ethyl 2-(2-chlorothiazol-4-yl)-4-(2-chloro-4-fluorophenyl)-6-methyl-1,4-dihydro-pyrimidin-5-carboxylate

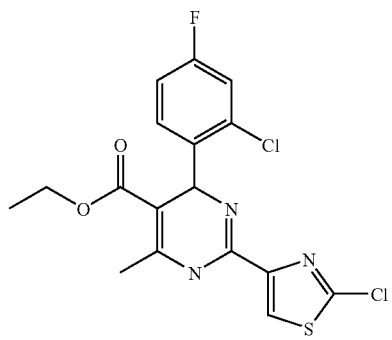

Step 1 Preparation of ethyl 2-chlorothiazol-4-carboxylate 17 g (100 mmol) ethyl 2-aminothiazol-4-carboxylate (Example 30, step 1) was added to 150 ml acetonitrile, and 18.5 g (110 mmol) dihydrated cupric chloride was added, and then, with mechanical stirring, 18.5 ml (130 mmol) isoamyl nitrite was slowly added dropwise, followed by continuing the reaction for 4 hr after complete of addition. To the resulting mixture, ethyl acetate and water were added, filtered to remove insoluble solids, and the layers were separated. The aqueous phase was further extracted with ethyl acetate, the resultant organic phases were combined, dried over anhydrous sodium sulfate, filtered, and concentrated to obtain 16 g of an oily liquid $^1$H NMR (CDCl$_3$) 1.39-1.43 (3H, t, J=7.0 Hz); 4.40-4.44 (2H, m, J=7.0 Hz); 8.08 (1H, s).

Step 2 Preparation of 2-chlorothiazol-4-carboxamide 16 g Ethyl 2-chlorothiazol-4-carboxylate was added to 120 ml ammonia water, and reacted for 3 hr. The resultant reaction mixture was extracted with ethyl acetate, dried over anhydrous sodium sulfate, filtered and concentrated to obtain 5.6 g of a colorless fine needle crystal (yield 34%); $^1$H NMR (DMSO-$d_6$) 7.66 (1H, s); 7.85 (1H, s); 8.24 (1H, s); $^{13}$C NMR (DMSO-$d_6$, ppm) 127.35, 148.47, 150.46, 161.06.

Step 3 Preparation of 2-chloro-4-cyanothiazole 5.6 g (34.4 mmol) 2-chlorothiazol-4-carboxamide was dissolved in 35 ml pyridine, and 13.1 g (68.8 mmol) p-tolylsulfonyl chloride was added, to carry out reaction overnight; and then, 150 ml ethyl acetate and 100 ml water were added to separate the layers. The resultant organic phase was washed with diluted HCl till aqueous phase being acidic, and then washed with saturated sodium chloride, dried over anhydrous sodium sulfate, filtered, concentrated and separated by a column chromatography to obtain 3.7 g 2-chloro-4-cyanothiazole (yield 75%) with mp 75-78° C., $^{13}$C NMR (CDCl$_3$, ppm) 112.73, 125.62, 132.38, 154.04; MS (EI) 144.0 (M$^+$).

Step 4 Preparation of 2-chlorothiazol-4-formamidine hydrochloride 10 mmol 2-chloro-4-cyanothiazole was dissolved in 10 ml anhydrous methanol, and 10 mmol sodium methoxide was added. Upon complete reaction of the starting materials, 20 mmol ammonium chloride was added, to carry out reaction in closed state for 12 hr. The reaction product was filtered to remove inorganic salt, and then the resultant filtrate was concentrated to obtain 2-chloro-4-thiazolformamidine hydrochloride.

Step 5 Preparation of ethyl 2-(2-chlorothiazol-4-yl)-4-(2-chloro-4-fluorophenyl)-6-methyl-1,4-dihydro-pyrimidin-5-carboxylate 2 mmol 2-chloro-4-thiazolformamidine hydrochloride, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.28 g of a yellowish crystal with mp 141-143° C.; $^1$H-NMR (400 MHz, DMSO-$d_6$) δ 1.01-1.05 (3H, m); 2.42 (3H, s); 3.92-3.95 (2H, m); 5.97 (1H, br); 7.16-7.40 (3H, m); 8.09 (1H, s); 9.52 (1H, s); MS (EI) 413.0 (M$^+$).

Example 34

Preparation of methyl 2-(2-chlorothiazol-4-yl)-4-(2-chloro-4-fluorophenyl)-6-methyl-1,4-dihydro-pyrimidin-5-carboxylate

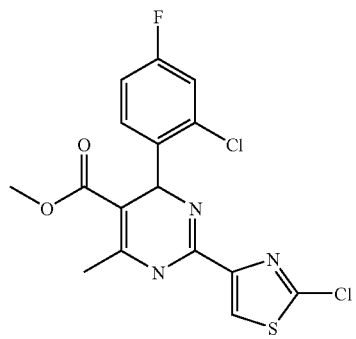

Using the method of Example 33, while using methyl acetoacetate in place of ethyl acetoacetate, 0.27 g of a yellow solid were obtained, with mp 160-162° C.; $^1$H-NMR (400 MHz, DMSO-$d_6$) δ 2.36-2.44 (3H, d); 3.48-3.50 (3H, d); 5.87-5.95 (1H, d); 7.15-7.40 (3H, m); 8.08-8.32 (1H, d); 9.2-9.57 (1H, d); MS (EI) 399.0 (M$^+$).

Example 35

Preparation of methyl 2-(5-chlorothiazol-4-yl)-4-(2-chloro-4-fluorophenyl)-6-methyl-1,4-dihydro-pyrimidin-5-carboxylate

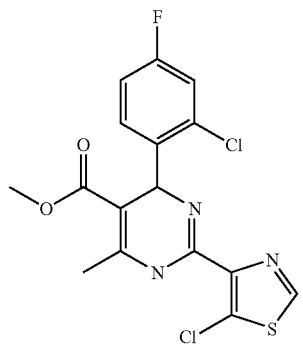

Using the method of Example 32, while using methyl acetoacetate in place of ethyl acetoacetate, 0.25 g of a yellowish solid was obtained, with mp 98-100° C.; $^1$H-NMR (400 MHz, DMSO-$d_6$) δ 2.24-2.43 (3H, m); 3.49-3.50 (3H, d); 6.01 (1H, s); 7.16-7.42 (3H, m); 9.08 (1H, s); 9.66 (1H, s); MS (EI) 398.9 (M$^+$).

Example 36

Preparation of methyl 2-(5-chlorothiazol-4-yl)-4-(4-fluorophenyl)-6-methyl-1,4-dihydro-pyrimidin-5-carboxylate

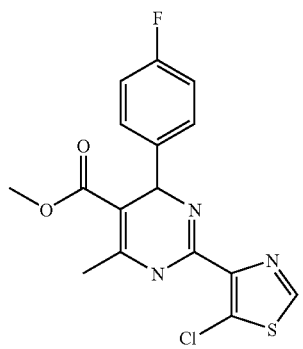

Using the method of Example 32, while using methyl acetoacetate in place of ethyl acetoacetate and using 4-fluorobenzaldehyde in place of 2-chloro-4-fluorobenzaldehyde, 0.24 g of a colorless solid was obtained, with mp 118-122° C.; $^1$H-NMR (400 MHz, DMSO-$d_6$) δ 2.36 (3H, s); 3.58 (3H, s); 5.45-5.65 (1H, m); 7.10-7.17 (2H, m); 7.31-7.35 (2H, m) 9.09-9.64 (2H, m); MS (EI) 365.0 (M$^+$).

Example 37

Preparation of methyl 2-(4-methylthiazol-5-yl)-4-(2-chloro-4-fluorophenyl)-6-methyl-1,4-dihydro-pyrimidin-5-carboxylate

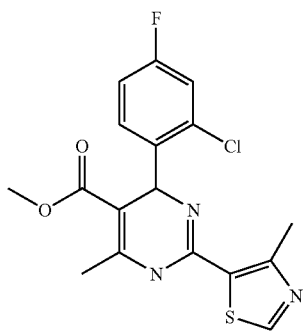

Step 1 Preparation of 4-methylthiazol-5-carboxamide 3.3 g (20 mmol) ethyl chloroacetoacetate and 1.8 g (30 mmol) thioformamide were dissolved in 40 ml ethanol, and reacted under reflux for 8 hr, followed by removing the solvent by rotation drying; and then, ethyl acetate and water were added to separate the layers. The resultant organic phase was dried over anhydrous sodium sulfate, filtered, and concentrated to obtain a red oily liquid. 60 ml ammonia water was directly added to the red oily liquid without purification, to carry out reaction in closed state for 24 hr. The reaction product was extracted with ethyl acetate, dried with sodium sulfate, filtered and concentrated to obtain 2.3 g of a solid (yield 82%).

Step 2 Preparation of 4-methyl-5-cyanothiazole 7.0 g (50 mmol) 4-Methylthiazol-5-carboxamide was dissolved in 50 ml pyridine, and 19 g (100 mmol) p-tolylsulfonyl chloride was added, to carry out reaction overnight; and then, 500 ml ethyl acetate and 150 ml water were added to separate the layers. The resultant organic phase was washed with diluted HCl till aqueous phase being acidic, and then washed with saturated sodium chloride, dried over anhydrous sodium sulfate, filtered and concentrated to obtain 2.2 g 4-methyl-5-cyanothiazole (yield 55%) with mp 32-34° C., $^1$H NMR (CDCl$_3$) 2.65 (3H, s); 8.88 (1H, s).

Step 3 Preparation of 4-methyl-5-thiazolformamidine acetate 1.6 g (12.9 mmol) 4-methyl-5-cyanothiazole was dissolved in 30 ml anhydrous methanol, the resultant solution was added dropwise into an anhydrous methanol solution of 2.7 g (38.8 mmol) hydroxylamine hydrochloride, and reacted at room temperature for 5 hr. The reaction product was filtered to remove insoluble matters, the resultant filtrate was concentrated to obtain an oily matter, then the oily matter was dispersed in water to precipitate a solid, which was filtered to obtain 1.2 g a fine needle crystal (yield 60%) with mp 153-154° C., $^1$H NMR (DMSO-d$_6$) 5.87 (2H, s), 8.91 (1H, s), 9.80 (1H, s); (D$_2$O) 2.36 (3H, s), 8.78 (1H, s); MS (FAB) 158.1 (M+1).

0.83 g (5.3 mmol) Amidoxime was dissolved in 25 ml glacial acetic acid, and 0.73 ml (7.7 mmol) acetic anhydride was added, to carry out reaction for 15 min; after complete reaction of the materials, 100 mg 10% Pd/C was added, and hydrogen was charged, to carry out reaction at normal pressure for 4 hr. The reaction product was filtered, the resultant filtrate was concentrated to nearly dry, and then acetone was added to precipitate a colorless crystal, which was filtered to obtain 0.7 g of 4-methyl-5-thiazolformamidine acetate (66%) with mp 182-184° C., $^1$H NMR (DMSO-d$_6$) 1.74 (3H, s); 2.53 (3H, s); 9.17 (1H, s); 10.04 (3H, br).

Step 4 Preparation of methyl 2-(4-methylthiazol-5-yl)-4-(2-chloro-4-fluorophenyl)-6-methyl-1,4-dihydro-pyrimidin-5-carboxylate 2 mmol 4-methyl-5-thiazolformamidine acetate, 2 mmol 2-chloro-4-fluorobenzaldehyde, 2 mmol methyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.24 g of a colorless crystal with mp 145-147° C.; $^1$H-NMR (400 MHz, DMSO-d$_6$) δ 2.34 (3H, s); 2.38 (3H, s); 3.50 (3H, s); 5.95 (1H, s); 7.12-7.49 (3H, m); 9.08 (1H, s); 9.61 (1H, s); MS (EI) 379.0 (M$^+$).

Example 38

Preparation of ethyl 2-(4-methylthiazol-5-yl)-4-(2-chloro-4-fluorophenyl)-6-methyl-1,4-dihydro-pyrimidin-5-carboxylate

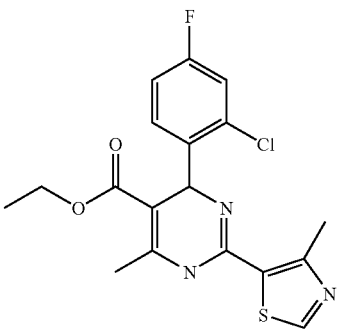

Using the method of Example 37, while using ethyl acetoacetate in place of methyl acetoacetate, 0.26 g of a colorless crystal was obtained, with mp 134-139° C.; $^1$H-NMR (400 MHz, DMSO-d$_6$) δ 1.02-1.05 (3H, m) 2.34

(3H, s); 2.38 (3H, s); 3.93-3.96 (2H, m); 5.96 (1H, s); 7.19-7.42 (3H, m); 9.01 (1H, s); 9.57 (1H, s); MS (EI) 393.0 (M+).

Example 39

Preparation of methyl 2-(2,4-dimethylthiazol-5-yl)-4-(2-chloro-4-fluorophenyl)-6-methyl-1,4-dihydro-pyrimidin-5-carboxylate

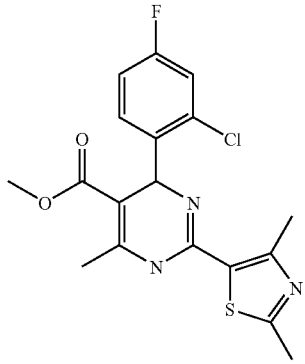

Using the method of Example 37, while using thioacetamide in place of thioformamide, 0.29 g of a colorless crystal was obtained, with mp 116-118° C.; $^1$H-NMR (400 MHz, DMSO-$d_6$) δ 2.26 (3H, s); 2.37 (3H, s); 2.58 (3H, s); 3.49 (3H, s); 5.95 (1H, s); 7.16-7.41 (3H, m); 9.51 (1H, s); MS (EI) 393.0 (M+).

Example 40

Preparation of ethyl 2-(2,4-dimethylthiazol-5-yl)-4-(2-chloro-4-fluorophenyl)-6-methyl-1,4-dihydro-pyrimidin-5-carboxylate

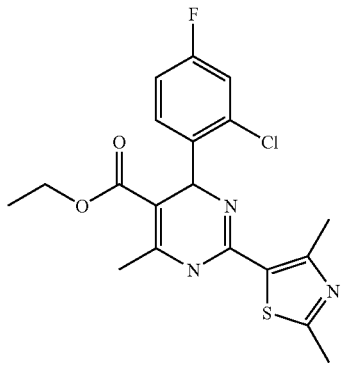

Using the method of Example 37, while using thioacetamide in place of thioformamide and using ethyl acetoacetate in place of methyl acetoacetate, 0.31 g of a colorless crystal was obtained, with mp 117-119° C.; $^1$H-NMR (400 MHz, DMSO-$d_6$) δ 1.01-1.05 (3H, m); 2.27 (3H, s); 2.37 (3H, s); 2.58 (3H, s); 3.92-3.96 (2H, m); 5.94 (1H, s); 7.17-7.41 (3H, m); 9.47 (1H, s); MS (EI) 407.0 (M+).

Example 41

Preparation of ethyl 2-(2-methylthiazol-5-yl)-4-(2-chloro-4-fluorophenyl)-6-methyl-1,4-dihydro-pyrimidin-5-carboxylate

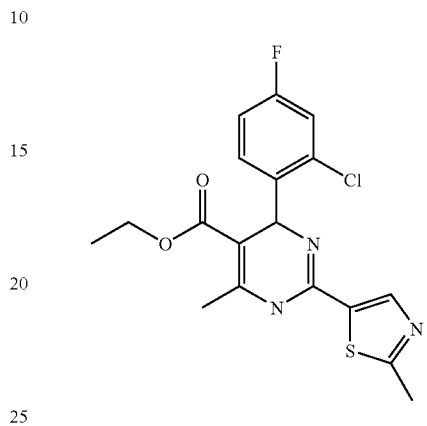

Step 1 Preparation of methyl 2-methylthiazol-5-carboxylate 2.0 g (14.6 mmol) methyl formylchloroacetate (A. Gangjee, A. Vidwans, E. Elzein, et. Al. J. Med. Chem. 2001, 44, 1993-2003), and 1.6 g (21.3 mmol) thioacetamide were dissolved in 10 ml water, heated, and reacted at 95° C. for 5 hr. The reaction product was extracted with ethyl acetate for 3 times, the ethyl acetate phases were combined, washed with a saturated sodium chloride solution, dried over anhydrous sodium sulfate, filtered, concentrated, and separated by a column chromatography to obtain 1.0 g methyl 2-methylthiazol-5-carboxylate (yield 43%), $^1$H NMR (CDCl3) 2.76 (3H, s), 3.89 (3H, s), 8.25 (1H, s).

Step 2 Preparation of 2-methyl-5-thiazolamide 1.4 g Methyl 2-methylthiazol-5-carboxylate was added to 25 ml ammonia water, to carry out reaction at room temperature for 3 hr. The reaction product was cooled down, filtered, and washed with water to obtain 0.95 g a white powdery solid (73%) with mp 202-205 (C.

Step 3 Preparation of 2-methyl-5-cyanothiazole 3.95 g (27.8 mmol) 2-Methyl-5-thiazolamide was dissolved in 22 ml pyridine, and 10.6 g (55.6 mmol) p-tolylsulfonyl chloride was added, to carry out reaction at 50 (C for 2 hr; and then, 250 ml ethyl acetate and water were added to separate the layers. The resultant organic phase was washed with diluted HCl till aqueous phase being acidic, and then washed with saturated sodium chloride, dried over anhydrous sodium sulfate, filtered, concentrated, and separated by a column chromatography to obtain 2.2 g 2-methyl-5-cyanothiazole (yield 65%), $^1$H NMR (CDCl$_3$) 2.80 (3H, s); 8.14 (1H, s).

Step 4 Preparation of 2-methylthiazol-5-formamidine acetate 4.2 g (33.9 mmol) 2-Methyl-5-cyanothiazole was dissolved in 30 ml anhydrous methanol, the resultant solution was added dropwise into an anhydrous methanol solution of 2.6 g (37.4 mmol) hydroxylamine hydrochloride, and reacted at room temperature for 5 hr. The reaction product was filtered to remove insoluble matters, the resultant filtrate was concentrated to obtain an oily matter, then ethyl ether was added in the oily matter to precipitate a solid, which was filtered to obtain 2.6 g amidoxime (yield 48%).

2.6 g (16.5 mmol) Amidoxime was dissolved in 50 ml glacial acetic acid, and 2.3 ml (24 mmol) acetic anhydride was added, to carry out reaction for 15 min; after complete reaction of the materials, 0.52 g 10% Pd/C was added, and hydrogen was charged, to carry out reaction at normal pressure for 4 hr. The reaction product was filtered, the resultant filtrate was concentrated to nearly dry, and then acetone was added to precipitate a solid, which was filtered to obtain 2.7 g of 2-methylthiazol-5-formamidine acetate (81%), with NMR (DMSO-$d_6$) 1.76 (3H, s); 2.71 (3H, s); 8.27 (1H, s); 9.65 (3H, br); MS (EI) 141 (M$^+$).

Step 5 Preparation of ethyl 2-(2-methylthiazol-5-yl)-4-(2-chloro-4-fluorophenyl)-6-methyl-1,4-dihydro-pyrimidin-5-carboxylate 2 mmol 2-Methylthiazol-5-formamidine acetate, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.24 g of a yellowish solid with mp 107-111° C.; $^1$H-NMR (400 MHz, DMSO-$d_6$) δ 1.0-1.04 (3H, m); 2.43 (3H, s); 2.59 (3H, s); 3.89-3.93 (2H, m); 5.90 (1H, s); 7.14-7.43 (3H, m); 9.52 (1H, s); MS (EI) 393.0 (M$^+$).

Example 42

Preparation of ethyl 2-(thiazol-5-yl)-4-(2-chloro-4-fluorophenyl)-6-methyl-1,4-dihydro-pyrimidin-5-carboxylate

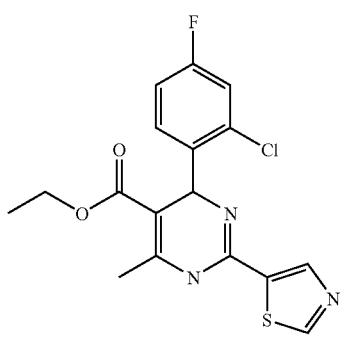

Using the method of Example 41, while using thioformamide in place of thioacetamide, 0.26 g of a yellowish crystal was obtained, with mp 121-125° C.; $^1$H-NMR (400 MHz, DMSO-$d_6$) δ 1.0-1.06 (3H, m); 2.44 (3H, s); 3.92-3.94 (2H, m); 5.93 (1H, s); 7.15-7.44 (3H, m); 8.54 (1H, d, J=0.56); 9.11 (1H, d, J=0.56); 9.6 (1H, s); MS (EI) 379.0 (M$^+$).

Example 43

Preparation of ethyl 2-(2-acetylaminothiazol-5-yl)-4-(2-chloro-4-fluorophenyl)-6-methyl-1,4-dihydro-pyrimidin-5-carboxylate

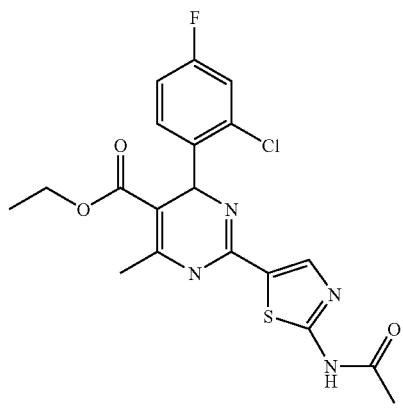

Step 1 Preparation of 2-amino-5-cyanothiazole 14 g (135 mmol) Formyl chloroacetonitrile (A. Gangjee, A. Vidwans, E. Elzein, et. Al. J. Med. Chem. 2001, 44, 1993-2003), and 10.3 g (135 mmol) thiourea were reacted in 75 ml water at 150° C. for 5 hr. The reaction product was extracted with ethyl acetate, dried, concentrated, and separated by a column chromatography to obtain 3.5 g of a solid (yield 21%), $^1$H NMR (DMSO-$d_6$) 7.83 (1H, s), 8.14 (2H, s).

Step 2 Preparation of 2-acetylamino-5-cyanothiazole 2.14 g 2-Amino-5-cyanothiazole was dissolved in 10 ml acetic acid, and 1.8 ml acetic anhydride was added to carry out reaction at 100° C. for 30 min. The reaction product was cooled down, and filtered to obtain 2.5 g of a clay-solid having metallic luster (yield 80%), $^1$H NMR (DMSO-$d_6$) 2.22 (3H, s), 8.36 (1H, s), 12.95 (1H, s).

Step 3 Preparation of 2-acetylaminothiazol-5-formamidine acetate 1.25 g 2-Acetylamino-5-cyanothiazole was dispersed in 60 ml methanol, 0.95 g hydroxylamine hydrochloride was added, to carry out reaction at room temperature for 24 hr. The reaction product was filtered, the solid matter obtained was dispersed in water, which was then filtered and washed with water to obtain 1.3 g powdery amidoxime, with $^1$H NMR (DMSO-$d_6$) 2.14 (3H, s), 5.94 (2H, s), 7.79 (1H, s), 9.63 (1H, s), 12.11 (1H, s).

1.14 g Amidoxime was dispersed in 30 ml acetic acid, and 0.52 ml acetic anhydride was added, to carry out reaction at room temperature for 1.5 hr; after complete reaction of the materials, 0.23 g 10% Pd/C was added, and hydrogen was charged, to carry out reaction at room temperature overnight. The reaction product was filtered, and the resultant filtrate was concentrated to obtain 1.1 g of a powdery solid 2-acetylaminothiazol-5-formamidine acetate.

Step 4 Preparation of ethyl 2-(2-acetylaminothiazol-5-yl)-4-(2-chloro-4-fluorophenyl)-6-methyl-1,4-dihydro-pyrimidin-5-carboxylate 2 mmol 2-Acetylaminothiazol-5-formamidine acetate, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.32 g of a yellowish solid with mp>250° C.; $^1$H-NMR (400 MHz, DMSO-$d_6$) δ 1.0-1.05 (3H, m); 2.14 (3H, s); 2.43 (3H, s); 2.59 (3H, s); 3.89-3.94 (2H, m); 5.89 (1H, s); 7.14-7.39 (3H, m); 8.11 (1H, s); 9.43 (1H, s); 12.22 (1H, br); MS (EI) 436.0 (M$^+$).

Example 44

Preparation of ethyl 2-(2-aminothiazol-5-yl)-4-(2-chloro-4-fluorophenyl)-6-methyl-1,4-dihydro-pyrimidin-5-carboxylate

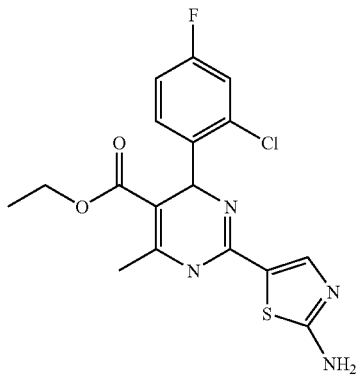

Ethyl 2-(2-acetylaminothiazol-5-yl)-4-(2-chloro-4-fluorophenyl)-6-methyl-1,4-dihydro-pyrimidin-5-carboxylate (Example 43) was refluxed with 6 mol/L HCl in ethanol to obtain 0.15 g a yellowish solid with mp 132-135° C.; $^1$H-NMR (400 MHz, DMSO-$d_6$) δ 1.0-1.05 (3H, m); 2.50 (3H, s); 3.90-3.93 (2H, m); 5.82 (1H, s); 7.13-7.50 (5H, m); 7.69 (1H, s); 9.19 (1H, s); MS (EI) 394.0 (M$^+$).

Example 45

Preparation of ethyl 2-(2-chlorothiazol-5-yl)-4-(2-chloro-4-fluorophenyl)-6-methyl-1,4-dihydro-pyrimidin-5-carboxylate

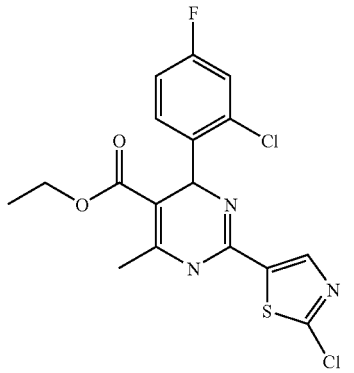

Step 1 Preparation of 2-chloro-5-cyanothiazole 3.4 g (27 mmol) 2-Amino-5-cyanothiazole (Example 43) and 5.1 g (30 mmol) dihydrated cupric chloride were dispersed in 100 ml acetonitrile. To the mixture, with vigorous stirring, 5.7 ml solution of isoamyl nitrite in acetonitrile was added rapidly dropwise over 30 min, followed by continuing the reaction for 10 hr. The reaction mixture was concentrated, dissolved in ethyl acetate, and filtered to remove insoluble matters. The organic phase was concentrated, and separated by a column chromatography to obtain 2.6 g of a liquid (yield 67%), which was placed aside to precipitate a needle crystal with mp 54-57° C., $^{13}$C NMR (CDCl$_3$, ppm) 108.16, 110.41, 150.59, 157.36; MS (EI) 144.1 (M$^+$).

Step 2 Preparation of 2-chlorothiazol-5-formamidine hydrochloride 0.43 g 2-chloro-5-cyanothiazole was dissolved in 8 ml anhydrous methanol, and 0.16 g sodium methoxide was added, to carry out the reaction with stirring for 15 min; and then, 0.48 g ammonium chloride was added, to further carry out reaction in closed state for 24 hr; finally, the reaction product was filtered to remove insoluble matters, and the resultant filtrate was concentrated, and recrystallized from isopropanol to obtain 0.47 g a yellow crystalline solid (yield 79%).

Step 3 Preparation of ethyl 2-(2-chlorothiazol-5-yl)-4-(2-chloro-4-fluorophenyl)-6-methyl-1,4-dihydro-pyrimidin-5-carboxylate 2 mmol 2-chlorothiazol-5-formamidine hydrochloride, 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.29 g of a yellow crystal with mp 159-162° C.; $^1$H-NMR (400 MHz, DMSO-$d_6$) δ 1.0-1.03 (3H, m); 2.43 (3H, s); 3.92-3.95 (2H, m); 5.91 (1H, s); 7.16-7.41 (3H, m); 8.31 (1H, s); 9.69 (1H, s); MS (EI) 413.0 (M$^+$).

Example 46

Preparation of methyl 2-(2-chlorothiazol-5-yl)-4-(2-chloro-4-fluorophenyl)-6-methyl-1,4-dihydro-pyrimidin-5-carboxylate

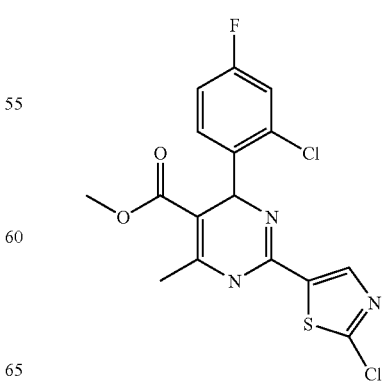

Using the method of Example 45, while using methyl acetoacetate in place of ethyl acetoacetate, 0.26 g of a yellow solid was obtained, with mp>230° C.; $^1$H-NMR (400 MHz, DMSO-d$_6$) δ 2.44 (3H, s); 3.48 (3H, s); 5.89 (1H, s); 7.15-7.41 (3H, m); 8.31 (1H, s); 9.73 (1H, s); MS (EI) 399.0 (M$^+$).

Example 47

Preparation of methyl 2-(2-chlorothiazol-5-yl)-4-(4-fluorophenyl)-6-methyl-1,4-dihydro-pyrimidin-5-carboxylate

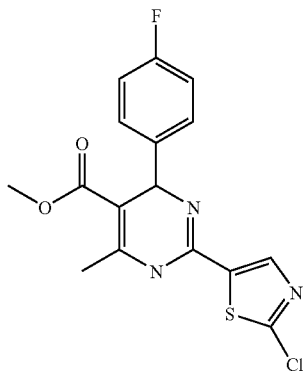

Using the method of Example 45, while using methyl acetoacetate in place of ethyl acetoacetate and using 4-fluorobenzaldehyde in place of 2-chloro-4-fluorobenzaldehyde, 0.23 g of a yellowish fine needle crystal was obtained, with mp 175-178° C.; $^1$H-NMR (400 MHz, DMSO-d$_6$) δ 2.38 (3H, s); 3.56 (3H, s); 5.53 (1H, s); 7.12-7.28 (4H, m); 8.33 (1H, s); 9.73 (1H, s); MS (EI) 365.0 (M$^+$).

Example 48

Preparation of ethyl 2-(1H-imidazol-2-yl)-4-(2-chloro-4-fluorophenyl)-6-methyl-1,4-dihydro-pyrimidin-5-carboxylate

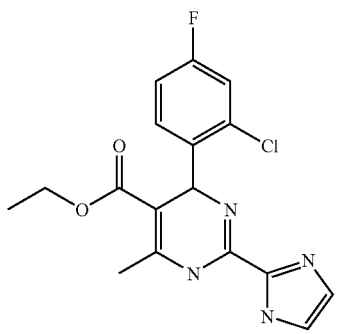

2 mmol 1H-imidazol-2-formamidine methane sulfonate (Tommasi, R. A., Macchia, W. M., Parker, D. T., Tetrahedron Lett 1998, 39:5947-5950), 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.19 g of a colorless fine needle crystal with mp 157-162° C.; $^1$H-NMR (400 MHz, DMSO-d$_6$) δ 1.02-1.06 (3H, t, J=7 Hz); 2.43 (3H, s); 3.91-3.93 (2H, m, J=7 Hz); 5.99 (1H, s); 7.04-7.42 (5H, m); 9.59 (1H, s); 12.69 (1H, s); MS (EI) 362.1 (M$^+$).

Example 49

Preparation of ethyl 2-(N-methyl-1H-imidazol-2-yl)-4-(2-chloro-4-fluorophenyl)-6-methyl-1,4-dihydro-pyrimidin-5-carboxylate

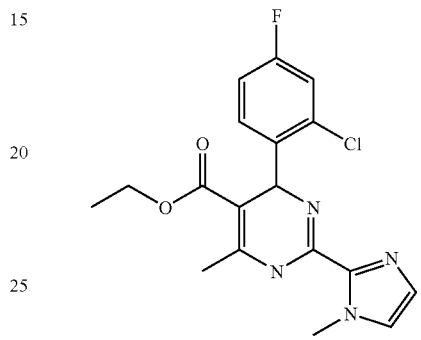

2 mmol N-methyl-1H-imidazol-2-formamidine methane sulfonate (Tommasi, R. A., Macchia, W. M., Parker, D. T., Tetrahedron Lett 1998, 39:5947-5950), 2 mmol 2-chloro-4-fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.23 g of a yellowish columnar crystal with mp 166-167° C.; $^1$H-NMR (400 MHz, DMSO-d$_6$) δ 1.03-1.06 (3H, m); 2.48 (3H, s); 3.81 (1H, s); 3.93-3.99 (2H, m); 6.00 (1H, s); 6.99-7.42 (5H, m); 9.57 (1H, s); MS (EI) 376.1 (M$^+$).

Example 50

Preparation of ethyl 2-(N-benzyl-1H-imidazol-2-yl)-4-(2-chloro-4-fluorophenyl)-6-methyl-1,4-dihydro-pyrimidin-5-carboxylate

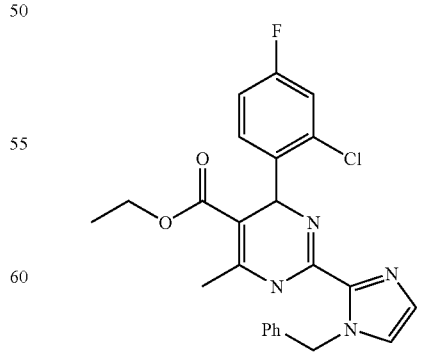

2 mmol N-benzyl-1H-imidazol-2-formamidine methane sulfonate (Tommasi, R. A., Macchia, W. M., Parker, D. T., Tetrahedron Lett 1998, 39:5947-5950), 2 mmol 2-chloro-4- fluorobenzaldehyde, 2 mmol ethyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.31 g of colorless granulates with mp 114-117° C.; $^1$H-NMR (400 MHz, DMSO-$d_6$) δ 1.0-1.05 (3H, m, J=7.0 Hz); 2.46 (3H, s); 3.91-3.96 (2H, m, J=7.0 Hz); 5.43-5.46 (1H, d, J=14.3 Hz); 5.81-5.85 (1H, d, J=14.3 Hz); 6.00 (1H, s); 6.92-7.5 (10H, m); 9.57 (1H, s); MS (EI) 452.1 (M$^+$).

Example 51

Preparation of ethyl 2-(N-benzyl-1H-imidazol-2-yl)-4-(4-fluorophenyl)-6-methyl-1,4-dihydro-pyrimidin-5-carboxylate

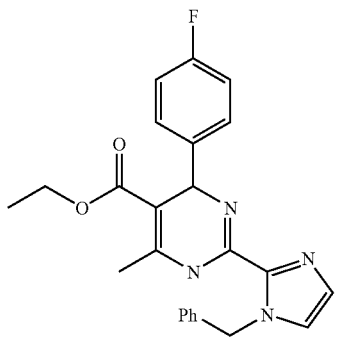

Using the method of Example 50, while using 4-fluorobenzaldehyde in place of 2-chloro-4-fluorobenzaldehyde, 0.26 g of a colorless fine needle crystal was obtained, with mp 162-164° C.; $^1$H-NMR (400 MHz, DMSO-$d_6$) δ 1.10-1.13 (3H, m J=7.28 Hz); 2.40 (3H, s); 4.0-4.03 (2H, m, J=7.28 Hz); 5.52-5.56 (1H, d, J=14.56 Hz); 5.62 (1H, s); 5.81-5.84 (1H, d, J=14.56 Hz); 6.99-7.56 (11H, m); 9.54 (1H, s); MS (EI) 418.2 (M$^+$).

Example 52

Preparation of ethyl 2-(N-methyl-1H-imidazol-2-yl)-4-(2-chlorophenyl)-6-methyl-1,4-dihydro-pyrimidin-5-carboxylate

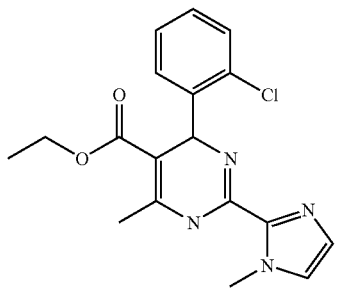

Using the method of Example 49, while using 2-chlorobenzaldehyde in place of 2-chloro-4-fluorobenzaldehyde, 0.27 g of a yellowish crystal was obtained, with mp 124-127° C.; $^1$H-NMR (400 MHz, DMSO-$d_6$) δ 1.02-1.06 (3H, t); 2.47 (3H, s); 3.81 (3H, s); 3.93-3.96 (2H, m); 6.03 (1H, s); 6.98 (1H, m); 7.22-7.45 (5H, m); 9.53 (1H, s); MS (EI) 358.0 (M$^+$).

Example 53

Preparation of ethyl 2-(N-methyl-1H-imidazol-2-yl)-4-(4-fluorophenyl)-6-methyl-1,4-dihydro-pyrimidin-5-carboxylate

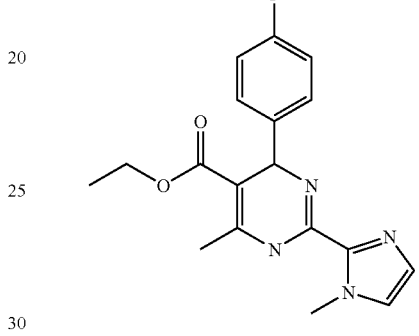

Using the method of Example 49, while using 4-fluorobenzaldehyde in place of 2-chloro-4-fluorobenzaldehyde, 0.24 g of a yellowish crystal was obtained, with mp 134-136° C.; $^1$H-NMR (400 MHz, DMSO-$d_6$) δ 1.12-1.16 (3H, m); 2.39 (3H, s); 3.86 (3H, s); 4.00-4.05 (2H, m); 5.67 (1H, s); 7.02-7.16 (3H, m); 7.29-7.40 (3H, m); 9.52 (1H, s); MS (EI) 342.3 (M$^+$).

Example 54

Preparation of ethyl 2-(1H-imidazol-2-yl)-4-(2-chlorophenyl)-6-methyl-1,4-dihydro-pyrimidin-5-carboxylate

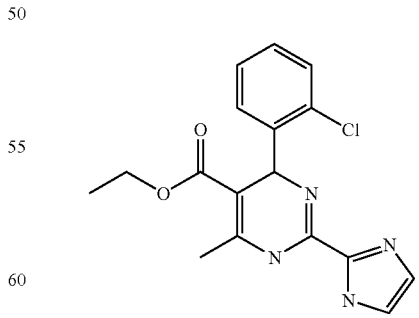

Using the method of Example 48, while using 2-chlorobenzaldehyde in place of 2-chloro-4-fluorobenzaldehyde, 0.22 g of a colorless solid was obtained, with mp 121-125° C.; $^1$H-NMR (400 MHz, DMSO-$d_6$) δ 1.01-1.05 (3H, t, J=7 Hz);

2.43 (3H, s); 3.91-3.94 (2H, m, J=7 Hz); 6.03 (1H, s); 7.04-7.38 (6H, m); 9.54 (1H, s); 12.67 (1H, s); MS (EI) 344.2 (M⁺).

Example 55

Preparation of methyl 2-(2,6-difluorophenyl)-4-(2-chloro-4-fluorophenyl)-6-methyl-1,4-dihydro-pyrimidin-5-carboxylate

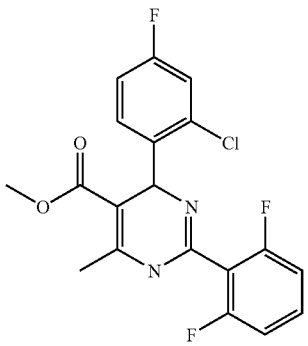

2 mmol 2,6-Difluorobenzamidine hydrochloride (Boere, R. J., Oakley, R. T., Read, R. V., J. Organometal. Chem. 1987, 331:161-167), 2 mmol 2-chloro-4-fluorobenzaldehyde, 2 mmol methyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.21 g of a colorless fine needle crystal with mp 126-128° C.; ¹H-NMR (400 MHz, DMSO-d₆) δ 2.87 (3H, s); 3.45 (3H, s); 5.92 (1H, s); 7.10-7.38 (6H, m); 9.87 (1H, s); MS (EI) 394.0 (M⁺).

Example 56

Preparation of ethyl 2-(2,6-difluorophenyl)-4-(2-chloro-4-fluorophenyl)-6-methyl-1,4-dihydro-pyrimidin-5-carboxylate

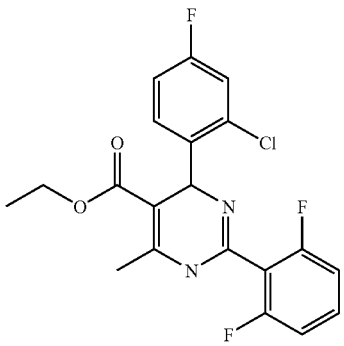

Using the method of Example 55, while using ethyl acetoacetate in place of methyl acetoacetate, 0.19 g of a colorless fine needle crystal was obtained, with mp 163-165° C.; ¹H-NMR (400 MHz, CDCl₃) δ 1.13-1.16 (3H, t, J=7.0 Hz); 2.44 (3H, s); 4.04-4.06 (2H, m, J=7.0 Hz); 6.17 (1H, s); 6.88-7.13 (4H, m); 7.31-7.46 (3H, m); MS (FAB) 409 (M+1).

Example 57

Preparation of isopropyl 2-(2,6-difluorophenyl)-4-(2-chloro-4-fluorophenyl)-6-methyl-1,4-dihydro-pyrimidin-5-carboxylate

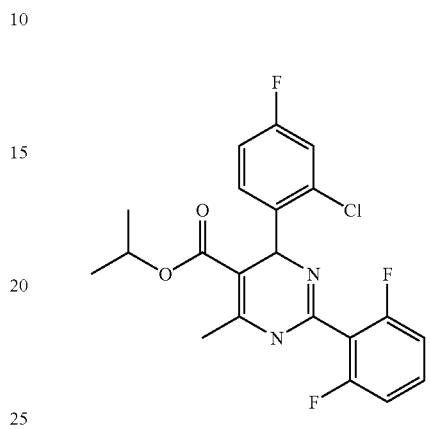

Using the method of Example 55, while using isopropyl acetoacetate in place of methyl acetoacetate, 0.14 g of a white flocculent solid was obtained, with mp 155-158° C.; ¹H-NMR (400 MHz, CDCl₃) δ 0.95-0.97 (3H, d, J=6.2 Hz); 1.21-1.22 (3H, d, J=6.2 Hz); 2.45 (3H, s); 4.92-4.95 (1H, m, J=6.2 Hz), 6.17 (1H, s); 6.88-7.01 (3H, m); 7.10-7.12 (1H, m); 7.33-7.47 (2H, m); MS (FAB) 423.1 (M+1).

Example 58

Preparation of ethyl 2-(2,4,6-trifluorophenyl)-4-(2-chloro-4-fluorophenyl)-6-methyl-1,4-dihydro-pyrimidin-5-carboxylate

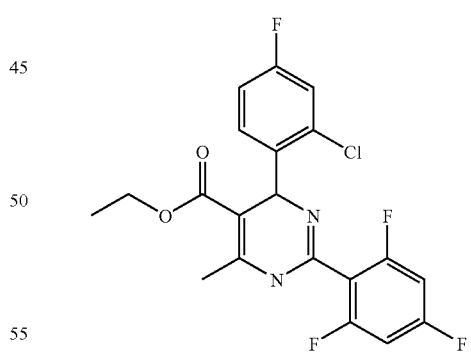

2 mmol 2,4,6-Trifluorobenzamidine acetate (Judkins, B. D., Allen, D. G., Cook, T. A. Synth. Commun. 1996, 26(23): 4351-4367), 2 mmol 2-chloro-4-fluorobenzaldehyde, 2 mmol methyl acetoacetate and 2.2 mmol sodium acetate were reacted under reflux in 10 ml anhydrous ethanol for 20 hr, concentrated, and then ethyl acetate and water were added to separate the layers. The ethyl acetate layer was dried over anhydrous sodium sulfate, and separated by a column chromatography to obtain 0.29 g of a colorless fine needle crystal with mp 184-186° C.; ¹H-NMR (400 MHz, DMSO-d₆) δ

1.02-1.05 (3H, t, J=7.3 Hz); 2.32 (3H, s); 3.92-3.95 (2H, m, J=7.3 Hz); 5.97 (1H, s); 7.21-7.45 (5H, m); MS (EI) 426 (M⁺).

Example 59

Preparation of methyl 2-(2,4,6-trifluorophenyl)-4-(2-chloro-4-fluorophenyl)-6-methyl-1,4-dihydro-pyrimidin-5-carboxylate

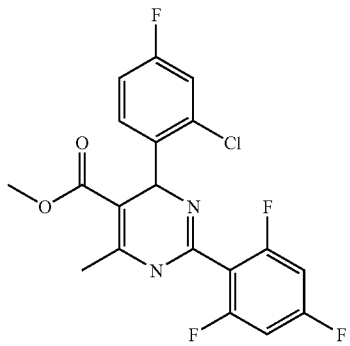

Using the method of Example 58, while using methyl acetoacetate in place of ethyl acetoacetate, 0.27 g of a colorless crystal was obtained, with mp 112-114° C.; $^1$H-NMR (400 MHz, DMSO-d$_6$) δ 2.33 (3H, s); 3.51 (3H, s); 5.96 (1H, s); 7.20-7.43 (5H, m); 9.9 (1H, s); MS (EI) 412 (M⁺).

Example 60

Preparation of R,R-N-(1-phenylethyl)-4-(2-chloro-4-fluorophenyl)-2-(2,4,6-trifluorophenyl)-6-methyl-1,4-dihydro-pyrimidin-5-carboxamide

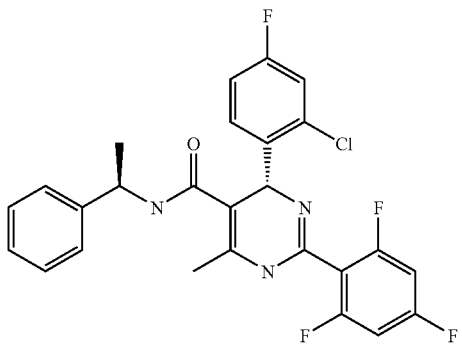

1.58 g (10 mmol) 2-chloro-4-fluorobenzaldehyde and 2.04 g (10 mmol) R-N-(1-phenylethyl)acetylacetamide were dissolved in 40 ml ethanol, and stirred at room temperature for 2 d; and then, 2.34 g (10 mmol) 2,4,6-trifluorobenzamidine acetate was added, to carry out reaction under reflux overnight. After removing the solvent by evaporation, ethyl acetate and water were added to separate the layers. The resultant ethyl acetate layer was dried over anhydrous sodium sulfate, filtered, concentrated, and separated by a column chromatography to obtain 4.7 g of a mixture. The mixture was dissolved in ethyl acetate to precipitate a solid, which was recrystallized from 50% ethanol to obtain a colorless fine needle crystal with $^1$H-NMR (400 MHz, DMSO-d$_6$) δ 1.3- 1.33 (3H, m); 1.97 (3H, s); 4.81-4.88 (1H, m); 5.96 (1H, s); 7.04-7.39 (9H, m); 7.57-7.61 (1H, m); 8.11-8.13 (1H, d); 9.25 (1H, s); MS (EI) 501 (M⁺).

Example 61

Preparation of R,R-N-(1-phenylethyl)-N-1-acetyl-4-(2-chloro-4-fluorophenyl)-2-(2,4,6-trifluorophenyl)-6-methyl-1,4-dihydro-pyrimidin-5-carboxamide

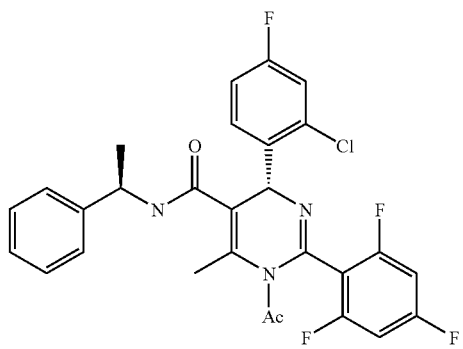

Using the method of Example 7, a colorless fine needle crystal was obtained from the compound of Example 60. $^1$H-NMR (400 MHz, DMSO-d$_6$) δ 1.39-1.41 (3H, d, J=7.0); 2.07 (3H, s); 2.10 (3H, s); 4.95-4.99 (1H, m); 6.47 (1H, s); 7.08-7.30 (8H, m); 7.45-7.51 (2H, m); 8.70-8.72 (1H, d, J=8.12); MS (EI) 543 (M⁺).

Example 62

Preparation of ethyl 4-R-(2-chloro-4-fluorophenyl)-2-(2,4,6-trifluorophenyl)-6-methyl-1,4-dihydro-pyrimidin-5-carboxylate

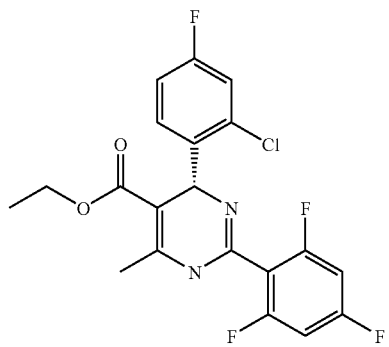

(−)-enantiomer of the compound of Example 58, and obtained by chiral separation as a colorless needle crystal. $^1$H-NMR (400 MHz, DMSO-d$_6$) δ 1.02-1.05 (3H, t, J=7.0 Hz); 2.32 (3H, s); 3.92-3.96 (2H, m, J=7.0 Hz); 5.97 (1H, s); 7.21-7.45 (5H, m); 9.86 (1H, s); MS (EI) 426 (M⁺); [α]$_D$=−92.38 (methanol).

Example 63

Determination of Cytotoxicity and Antiviral Activity of the Selected Compounds The cytotoxicity and antiviral activity of the compounds according to this invention were determined in accordance with the methods described above, and the results were showed in Table 1.

TABLE 1

Inhibitory effects of the selected compounds on HBV DNA

| Example No. | $IC_{50}$ μM | $TD_{50}$ μM |
| --- | --- | --- |
| 1 | 3.35 | 50.59 |
| 28 | 3.99 | 58.50 |
| 29 | 8.42 | 56.34 |
| 33 | 0.87 | 7.17 |
| 34 | 2.08 | 12.35 |
| 37 | 14.55 | 101.42 |
| 38 | 2.22 | 54.33 |
| 39 | 3.20 | 165.90 |
| 40 | 2.59 | 157.42 |
| 42 | 3.61 | >32.90 |
| 43 | 2.29 | 76.43 |
| 44 | 2.69 | 22.56 |
| 49 | 0.27 | 38.83 |
| 51 | 6.65 | 36.87 |
| 53 | 10.23 | 281.14 |
| 55 | 4.01 | 60.84 |
| 56 | 2.03 | 117.50 |
| 58 | 2.60 | 32.50 |
| 59 | 3.39 | >30.30 |
| 62 | 2.01 | 117.23 |

What is claimed is:

1. A compound of formula (I)

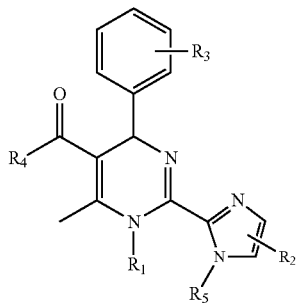

(I)

or a pharmaceutically acceptable salt thereof,
wherein
$R^1$ represents hydrogen, $(C_1-C_4)$-alkyl, $(C_2-C_4)$-alkenyl, $(C_2-C_6)$-acyl or benzoyl,
$R^2$ represents one or more substituents independently selected from: hydrogen, halogen, hydroxyl, cyano, trifluoromethyl, nitro, benzyl, $(C_1-C_6)$-alkyl, $(C_1-C_6)$-alkoxy, $(C_1-C_6)$-alkylthio, $(C_1-C_6)$-alkoxycarbonyl, $(C_1-C_6)$-acyloxy, amino, $(C_1-C_6)$-alkylamino, $(C_1-C_6)$-dialkylamino, or $(C_1-C_6)$-acylamino,
$R^3$ represents one or more substituents independently selected from: hydrogen, halogen, trifluoromethyl, trifluoromethoxy, trifluoromethylsulfonyl, nitro, cyano, carboxy, hydroxyl, $(C_1-C_6)$-alkoxy, $(C_1-C_6)$-alkoxycarbonyl and $(C_1-C_6)$-alkyl, wherein said alkyl may be substituted by aryl having from 6 to 10 carbon atoms, halogen, or a group presented by formulae —S—$R^6$, $NR^7R^8$, CO—$NR^9R^{10}$ and -A-$CH_2$—$R^{11}$,
wherein
$R^6$ represents phenyl optionally substituted by halogen,
$R^7$, $R^8$, $R^9$ and $R^{10}$, the same or different, respectively represent hydrogen, phenyl, hydroxyl-substituted phenyl, hydroxyl, $(C_1-C_6)$-acyl or $(C_1-C_6)$-alkyl, wherein said alkyl may be substituted by hydroxyl, halogen, $(C_1-C_6)$-alkoxycarbonyl, phenyl or hydroxyl-substituted phenyl,
A represents O, S, SO or $SO_2$,
$R^{11}$ represents phenyl optionally substituted with one or more groups independently selected from: halogen, nitro, trifluoromethyl, $(C_1-C_6)$-alkyl and $(C_1-C_6)$-alkoxy,
$R^4$ represents a group represented by formula —$XR^{12}$ or —$NR^{13}R^{14}$,
wherein
X represents oxygen or a bond,
$R^{12}$ represents hydrogen, a straight or branched $(C_1-C_6)$-alkoxycarbonyl, or a straight, branched or cyclic, saturated or unsaturated $(C_1-C_8)$-hydrocarbyl, wherein said hydrocarbyl optionally includes one or two identical or different heterochain unit(s) selected from the group consisting of O, CO, NH, —NH$(C_1-C_4)$-alkyl, —N$((C_1-C_4)$-alkyl$)_2$, S and $SO_2$, and may be optionally substituted by halogen, nitro, cyano, hydroxyl, aryl having from 6 to 10 carbon atoms, aralkyl, heteroaryl or a group represented by formula —$NR^{15}R^{16}$,
wherein
$R^{15}$ and $R^{16}$, the same or different, respectively represent hydrogen, benzyl or $(C_1-C_6)$-alkyl,
$R^{13}$ and $R^{14}$, the same or different, respectively represent hydrogen, benzyl, $(C_1-C_6)$-alkyl, or cycloalkyl having from 3 to 6 carbon atoms,
$R^5$ represents hydrogen, benzyl, $(C_1-C_6)$-alkyl, wherein said alkyl may be substituted by hydroxyl, halogen, $(C_1-C_6)$-alkoxycarbonyl, phenyl or substituted phenyl.

2. The compound of formula (I) according to claim 1, selected from a group consisting of:

(1) Ethyl 2-(1H-imidazol-2-yl)-4-(2-chloro-4-fluorophenyl)-6-methyl-1,4-dihydro-pyrimidin-5-carboxylate;

(2) Ethyl 2-(N-methyl-1H-imidazol-2-yl)-4-(2-chloro-4-fluorophenyl)-6-methyl-1,4-dihydro-pyrimidin-5-carboxylate;

(3) Ethyl 2-(N-benzyl-1H-imidazol-2-yl)-4-(2-chloro-4-fluorophenyl)-6-methyl-1,4-dihydro-pyrimidin-5-carboxylate;

(4) Ethyl 2-(N-benzyl-1H-imidazol-2-yl)-4-(4-fluorophenyl)-6-methyl-1,4-dihydro-pyrimidin-5-carboxylate;

(5) Ethyl 2-(N-methyl-1H-imidazol-2-yl)-4-(2-chlorophenyl)-6-methyl-1,4-dihydro-pyrimidin-5-carboxylate;

(6) Ethyl 2-(N-methyl-1H-imidazol-2-yl)-4-(4-fluorophenyl)-6-methyl-1,4-dihydro-pyrimidin-5-carboxylate; and (7) Ethyl 2-(1H-imidazol-2-yl)-4-(2-chlorophenyl)-6-methyl-1,4-dihydro-pyrimidin-5-carboxylate;

or a pharmaceutically acceptable salt thereof.

3. A compound of formula (I)

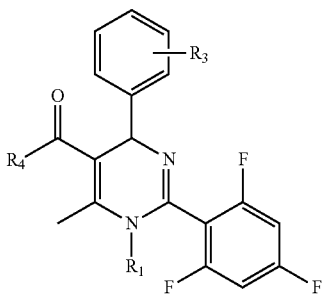

(I)

or a pharmaceutically acceptable salt thereof,
wherein
$R^1$ represents hydrogen, $(C_1$-$C_4)$-alkyl, $(C_2$-$C_4)$-alkenyl, $(C_2$-$C_6)$-acyl or benzoyl,
$R^3$ represents one or more substituents independently selected from: hydrogen, halogen, trifluoromethyl, trifluoromethoxy, trifluoromethylsulfonyl, nitro, cyano, carboxy, hydroxy, $(C_1$-$C_6)$-alkoxy, $(C_1$-$C_6)$-alkoxycarbonyl and $(C_1$-$C_6)$-alkyl, wherein said alkyl may be substituted by aryl having from 6 to 10 carbon atoms, halogen, or a group presented by formulae —S—$R^6$, $NR^7R^8$, CO—$NR^9R^{10}$ and -A-$CH_2$—$R^{11}$,
wherein
$R^6$ represents phenyl optionally substituted by halogen,
$R^7$, $R^8$, $R^9$ and $R^{10}$, the same or different, respectively represent hydrogen, phenyl, hydroxy-substituted phenyl, hydroxyl, $(C_1$-$C_6)$-acyl or $(C_1$-$C_6)$-alkyl, wherein said alkyl may be substituted by hydroxyl, halogen, $(C_1$-$C_6)$-alkoxycarbonyl, phenyl or hydroxyl-substituted phenyl,
A represents O, S, SO or $SO_2$,
$R^{11}$ represents phenyl optionally substituted with one or more groups independently selected from: halogen, nitro, trifluoromethyl, $(C_1$-$C_6)$-alkyl and $(C_1$-$C_6)$-alkoxy, $R^4$ represents a group represented by formula —$XR^{12}$ or —$NR^{13}R^{14}$,
wherein
X represents oxygen or a bond,
$R^{12}$ represents hydrogen, a straight or branched $(C_1$-$C_6)$-alkoxycarbonyl, or a straight, branched or cyclic, saturated or unsaturated $(C_1$-$C_8)$-hydrocarbyl, wherein said hydrocarbyl optionally includes one or two identical or different heterochain unit(s) selected from the group consisting of O, CO, NH, —NH$(C_1$-$C_4)$-alkyl, —N$((C_1$-$C_4)$-alkyl$)_2$, S and $SO_2$, and may be optionally substituted by halogen, nitro, cyano, hydroxyl, aryl having from 6 to 10 carbon atoms, aralkyl, heteroaryl or a group represented by formula —$NR^{15}R^{16}$,
wherein
$R^{15}$ and $R^{16}$, the same or different, respectively represent hydrogen, benzyl or $(C_1$-$C_6)$-alkyl,
$R^{13}$ and $R^{14}$, the same or different, respectively represent hydrogen, benzyl, $(C_1$-$C_6)$-alkyl, or cycloalkyl having from 3 to 6 carbon atoms.

4. The compound of formula (I) according to claim 3, selected from a group consisting of:
(1) Ethyl 2-(2,4,6-trifluorophenyl)-4-(2-chloro-4-fluorophenyl)-6-methyl-1,4-dihydro-pyrimidin-5-carboxylate;
(2) Methyl 2-(2,4,6-trifluorophenyl)-4-(2-chloro-4-fluorophenyl)-6-methyl-1,4-dihydro-pyrimidin-5-carboxylate;
(3) R,R-N-(1-phenylethyl)-4-(2-chloro-4-fluorophenyl)-2-(2,4,6-trifluorophenyl)-6-methyl-1,4-dihydro-pyrimidin-5-carboxamide;
(4) R,R-N-(1-phenylethyl)-N-1-acetyl-4-(2-chloro-4-fluorophenyl)-2-(2,4,6-trifluorophenyl)-6-methyl-1,4-dihydro-pyrimidin-5-carboxamide; and
(5) Ethyl 4-R-(2-chloro-4-fluorophenyl)-2-(2,4,6-trifluorophenyl)-6-methyl-1,4-dihydro-pyrimidin-5-carboxylate,
or a pharmaceutically acceptable salt thereof.

* * * * *

UNITED STATES PATENT AND TRADEMARK OFFICE
CERTIFICATE OF CORRECTION

PATENT NO. : 8,168,642 B2  
APPLICATION NO. : 12/373183  
DATED : May 1, 2012  
INVENTOR(S) : Song Li et al.

Page 1 of 1

It is certified that error appears in the above-identified patent and that said Letters Patent is hereby corrected as shown below:

In the Claims

In column 53, claim 3, line 19, before "hydrogen, $(C_1$-$C_4)$" replace "re resents" with --represents--.

Signed and Sealed this  
Seventh Day of August, 2012

David J. Kappos  
*Director of the United States Patent and Trademark Office*